US007133781B2

(12) United States Patent
Toll et al.

(10) Patent No.: US 7,133,781 B2
(45) Date of Patent: Nov. 7, 2006

(54) BIOPOLYMER SEQUENCE COMPARISON

(75) Inventors: Lawrence R. Toll, Redwood City, CA (US); Patrick Denis Lincoln, Woodside, CA (US); Peter D. Karp, San Mateo, CA (US); Kemal Sonmez, Menlo Park, CA (US)

(73) Assignee: SRI International, Menlo Park, CA (US)

( * ) Notice: Subject to any disclaimer, the term of this patent is extended or adjusted under 35 U.S.C. 154(b) by 0 days.

(21) Appl. No.: 10/006,492

(22) Filed: Dec. 3, 2001

(65) Prior Publication Data

US 2002/0146724 A1 Oct. 10, 2002

Related U.S. Application Data

(60) Provisional application No. 60/250,743, filed on Dec. 1, 2000.

(51) Int. Cl.
*G06F 19/00* (2006.01)
*G01N 33/48* (2006.01)

(52) U.S. Cl. .......................................... 702/20; 702/19
(58) Field of Classification Search .................. 702/19, 702/20; 704/243, 251–256
See application file for complete search history.

(56) References Cited

U.S. PATENT DOCUMENTS

| 5,568,563 | A | 10/1996 | Tanaka et al. |
| 5,701,256 | A | 12/1997 | Marr et al. |
| 5,873,052 | A | 2/1999 | Sharaf |
| 6,128,587 | A | 10/2000 | Sjolander |
| 6,314,434 | B1 | 11/2001 | Shigemi et al. |
| 6,438,496 | B1 | 8/2002 | Yoshida et al. ............... 702/19 |

OTHER PUBLICATIONS

Baldi, P. et al., "Hidden Markov Models of Biological Primary Sequence Information", *Proc. Natl. Acad. Sci. USA*, vol. 91, pp. 1059-1063; Feb. 1994.
Barrett, C. et al. "Scoring Hidden Markov Models", *CABIOS*, vol. 13, No. 2, pp. 191-199; 1997.
Brakch, N. et al. "Favourable Side-Chain Orientation of Cleavage Site Dibasic Residues of Prohormone in Proteolytic Processing by Prohormone Convertase 1/3", *Eur. J. biochem*. vol. 267, pp. 1626-1632; 2000.
Brown, M. et al., "Using Dirichlet Mixture Priors to Derive Hidden Markov Models for Protein Families", *Proc. of First Int. Conf. on Intelligent Systems for Molecular Biology*, pp. 47-55, Menlo Park, CA, Jul. 1993. AAAI/MIT Press.

Chesneau, V. et al., "N-Arginine Diabasic Convertase (NRD Convertase): A Newcomer to the Family of Processing Endopeptidases", *Biochimic* vol. 76, pp. 234-240; Paris, Mar. 1994.
Chou, K-C. et al., "Studies on the Specificity of HIV Protease: An Application of Markov Chain Theory", *Journal of Protein Chemistry*, vol. 12, No. 6, pp. 709-724; 1993.
Chou, K-C., "Prediction of Human Immunodeficiency Virus Protease Cleavage Sites in Protein", *Analytical Biochemistry* vol. 233, pp. 1-14; 1996.
Chou, K-C. et al., "Predicting Human Immunodeficiency Virus Protease Cleavage Sites in Proteins by a Discriminant Function Method", *Proteins:Structure, Function, and Genetics* vol. 24, pp. 51-72; 1996.
Grice, JA. Et al., "Reduced Space Sequence Alignment", *CABIOS*, vol. 13, pp. 45-53, 1997.
Hughey, R. et al., "Hidden Markov Models for Sequence Analysis: Extension and Analysis of the Basic Method", Reprint *CABIOS* vol. 12, pp. 95-107, 1996.
Hughey, R. et al., "SAM : Sequence Alignment and Modeling software System", *Technical Report UCSC-CRL-96-22*, University of California, Santa Cruz, CA, Jul. 1998.
Hughey, R., "Massively Parallel Biosequence Analysis.", *Technical Report UCSC-CRL-93-14*, University of California, Santa Cruz, CA, Apr. 1993.
Jagla, B. et al., "Adaptive Encoding Neural Networks for the Recognition of Human Signal Peptide Cleavage Sites" *BIO*, vol. 16, No. 3, Mar. 2000.
Karchin, R., "Hidden Markov Models and Protein Sequence Analysis" from http://www.cse.ucsc.edu/research/compbio/ismb99.handouts//KK185FP.html printed from webiste Mar. 14, 2002.
Karplus, K. et al., "Hidden Markov Models for Detecting Remote Protein Homologies", *BIO Informatics*. vol. 14, No. 10, pp. 846-856; Oct. 1998.
Karplus, K. et al., "Predicting Protein Structure Using Hidden Markov Models", *Proteins:Structure, Function, and Genetic*, Suppl., pp. 134-139; Sep. 1997.
Krogh, A. et al., "Hidden Markov Models in Computational Biology. Applications to Protein Modeling", *J. Mol. Biol.* vol. 235, pp. 1501-1531; Feb. 1994.
Krogh, A. et al., Predicting Transmembrane Protein Topology with a Hidden Markov Model: Application to Complete Genomes *Journal of Molecular Biology* vol. 305, No. 3, pp. 567-580; 2001.

(Continued)

*Primary Examiner*—Marianne P. Allen
(74) *Attorney, Agent, or Firm*—Kin-Wah Tong, Esq.; Patterson & Sheridan, LLP

(57) ABSTRACT

Disclosed are methods, software, and systems for comparing biopolymer sequences. The model includes at least two different characterizations of states of matching between segments of sequences at defined positions. Examples of states of matching include: similarity and dissimilarity between objects, as well as similarity to a reference, e.g., a reference sequence or a sequence profile. A topology of particular match states can be used to identify classes of sequences, e.g., preprohormone sequences.

16 Claims, 7 Drawing Sheets

OTHER PUBLICATIONS

Ladunga, I., "Large-Scale Predictions of Secretory Proteins from Mammalian genomic and EST sequences" *Analytical Biotechnology*, pp. 13-18; 2000.

Lockless, SW. et al. "Evolutionarily Conserved Pathways of Energetic Connectivity in Protein Families", *Science* vol. 286, pp. 295-299; Oct. 1999.

Nielsen, H.et al., "Identification of Prokaryotic and Eukaryotic Signal Peptides and Prediction of Cleavage Sites", *Protein Engineering* vol. 10, No. 1, pp. 1-6; Jan. 1997.

Hielsen, H. et al. "Prediction of Signal Peptides and Signal Anchors by a Hidden Markov Model", *American Association for Artificial Intelligence ISMB*, pp. 122-130; 1998.

Nielsen, H. et al. "Machine Learning Approaches for the Prediction of Signal Peptides and Other Protein Sorting Signals", *Protein Engineering* vol. 12, No. 1, pp. 3-9; Jan. 1999.

Paracel, "Hidden Markov Model", from http://paracel.com/publications/hmm_white_paper.html printed from website Mar. 14, 2002.

Rabiner, LR., "A Tutorial on Hidden Markov Models and Selected Applications in Speech Recognition", *Proceedings of the IEEE*, vol. 77, No. 2, pp. 257-186; Feb . 1989.

Rholam, M. et al., "Role of Amino Acid Sequences Flanking Dibasic Cleavage Sites in Precursor Proteolytic Processing. The Importance of the First Residue C-terminal of the cleavage site", *Eur. J. Biochem*. vol. 277, pp. 707-714; Feb. 1995.

UCSC Comp. Biol. Group, "Sequence Alignment and Modeling System" from http://www.cse.ucsc.edu/research/compbio/sam.html printed from website Mar. 14, 2002.

Bucher, P. et al., "A Flexible Motif Search Technique based on Generalized Profiles," Computers and Chemistry, vol. 20, pp. 3-24, Jan. 1996.

Eddy, S.R., "Hidden Markov Models," Current Opinion in Structural Biology, vol. 6, pp. 361-365, 1996.

Eddy, S., "Profile Hidden Markov Models," Bioinformatics Review, 14(9), pg. 755-763, 1998.

Eddy, et al., "Maximum Discrimination Hidden Markov Models of Sequence Consensus," J. Computational Biology, 2(1), pp. 9-23, 1995.

Eddy, S.R., "Multiple Alignment Using Hidden Markov Models," Proc. Third In. Conf. Intelligent Systems for Molecular Biology, AAAI Press, Menlo Park, pp. 114-120, PostScript; 1995.

Grate, et al., "Tutorial Stechastis Modeling Techniques: Understanding and Using Hidden Markov Models," University of California, Santa Cruz, CA pp. 1-34, Jun. 1996; www.cse.ucsc.edu/research/compbio/sam.html; Tutorial allegedly used at ISMB, Jun. 1996.

Grundy et al., "Meta-MEME. Motif-Based Hidden Markov Models of Protein Families," Computer Applications.

Karchin et al., "Weighting Hidden Markov Models for Maximum Discrimination," Bioinformatics, 14(9), pp. 772-782, 1998.

McClure, et al., "Parameterization studies from the SAM and HMMER methods of hidden Markov Model," Proc. Fourth Int. Conf. Intelligent Systems to Molecular Biology 155-164 UNLV, Las Vegas, 1996.

Tarnas, et al., "Reduced space hidden Markov model training," Bioinformatics, 14(5), 401 406, 1998.

|   | A | C | D | E | F | G | H | I | K | L | M | N | P | Q | R | S | T | V | W | Y |
|---|---|---|---|---|---|---|---|---|---|---|---|---|---|---|---|---|---|---|---|---|
| A | 4 |   |   |   |   |   |   |   |   |   |   |   |   |   |   |   |   |   |   |   |
| C | 0 | 9 |   |   |   |   |   |   |   |   |   |   |   |   |   |   |   |   |   |   |
| D | -2 | -3 | 6 |   |   |   |   |   |   |   |   |   |   |   |   |   |   |   |   |   |
| E | -1 | -4 | 2 | 5 |   |   |   |   |   |   |   |   |   |   |   |   |   |   |   |   |
| F | -2 | -2 | -3 | -3 | 6 |   |   |   |   |   |   |   |   |   |   |   |   |   |   |   |
| G | 0 | -3 | -1 | -2 | -3 | 6 |   |   |   |   |   |   |   |   |   |   |   |   |   |   |
| H | -2 | -3 | -1 | 0 | -1 | -2 | 8 |   |   |   |   |   |   |   |   |   |   |   |   |   |
| I | -1 | -1 | -3 | -3 | 0 | -4 | -3 | 4 |   |   |   |   |   |   |   |   |   |   |   |   |
| K | -1 | -3 | -1 | 1 | -3 | -2 | -1 | -3 | 5 |   |   |   |   |   |   |   |   |   |   |   |
| L | -1 | -1 | -4 | -3 | 0 | -4 | -3 | 2 | -2 | 4 |   |   |   |   |   |   |   |   |   |   |
| M | -1 | -1 | -3 | -2 | 0 | -3 | -2 | 1 | -1 | 2 | 5 |   |   |   |   |   |   |   |   |   |
| N | -2 | -3 | 1 | 0 | -3 | 0 | 1 | -3 | 0 | -3 | -2 | 6 |   |   |   |   |   |   |   |   |
| P | -1 | -3 | -1 | -1 | -4 | -2 | -2 | -3 | -1 | -3 | -2 | -2 | 7 |   |   |   |   |   |   |   |
| Q | -1 | -3 | 0 | 2 | -3 | -2 | 0 | -3 | 1 | -2 | 0 | 0 | -1 | 5 |   |   |   |   |   |   |
| R | -1 | -3 | -2 | 0 | -3 | -2 | 0 | -3 | 2 | -2 | -1 | 0 | -2 | 1 | 5 |   |   |   |   |   |
| S | 1 | -1 | 0 | 0 | -2 | 0 | -1 | -2 | 0 | -2 | -1 | 1 | -1 | 0 | -1 | 4 |   |   |   |   |
| T | 0 | -1 | -1 | -1 | -2 | -2 | -2 | -1 | -1 | -1 | -1 | 0 | -1 | -1 | -1 | 1 | 5 |   |   |   |
| V | 0 | -1 | -3 | -2 | -1 | -3 | -3 | 3 | -2 | 1 | 1 | -3 | -2 | -2 | -3 | -2 | 0 | 4 |   |   |
| W | -3 | -2 | -4 | -3 | 1 | -2 | -2 | -3 | -3 | -2 | -1 | -4 | -4 | -2 | -3 | -3 | -2 | -3 | 11 |   |
| Y | -2 | -2 | -3 | -2 | 3 | -3 | 2 | -1 | -2 | -1 | -1 | -2 | -3 | -1 | -2 | -2 | -2 | -1 | 2 | 7 |

FIG. 5

Signal Sequence

Mouse MKILFCDVLLLSLLSSVFSSCPRDCLTCQEKLHPAPDSFNLKTCILQCEEKVFPRPLWTVCTKVMASG
Human MKVLLCDLLLLSLFSSVFSSCQRDCLTCQEKLHPALDSFDLEVCILECEEKVFPSPLWTPCTKVMARS Mouse SGQLSPADPELVSAALYQPKASEMQHLKRMPRVRSLVQVRDAEPGADAEPGADDAEEVEQK
Human SWQLSPAAPEHVAAALYQPRASEMQHLRRMPRVRSLFQEQ-------EEPEPGMEEAGEMEQK N/OFQ                                    Potential Hormones A                              B Mouse QLQKRFGGFTGARKSARKLANQKRFSEFMRQYLVLVLSMQSSQRRRTLHQNGNV      (SEQ ID NO:1)
Human QLQKRFGGFTGARKSARKLANQKRFSEFMRQYLVLVLSMQSSQRRRTLHQNGNV      (SEQ ID NO:2)

FIG. 6

SEQUENCE LISTING

<160> NUMBER OF SEQ ID NOS: 2

<210> SEQ ID NO 1
<211> LENGTH: 187
<212> TYPE: PRT
<213> ORGANISM: Mus musculus

<400> SEQUENCE: 1

Met Lys Ile Leu Phe Cys Asp Val Leu Leu Ser Leu Leu Ser Ser
1               5                   10                  15

Val Phe Ser Ser Cys Pro Arg Asp Cys Leu Thr Cys Gln Glu Lys Leu
                20                  25                  30

His Pro Ala Pro Asp Ser Phe Asn Leu Lys Thr Cys Ile Leu Gln Cys
            35                  40                  45

Glu Glu Lys Val Phe Pro Arg Pro Leu Trp Thr Val Cys Thr Lys Val
    50                  55                  60

Met Ala Ser Gly Ser Gly Gln Leu Ser Pro Ala Asp Pro Glu Leu Val
65                  70                  75                  80

Ser Ala Ala Leu Tyr Gln Pro Lys Ala Ser Glu Met Gln His Leu Lys
                85                  90                  95

Arg Met Pro Arg Val Arg Ser Leu Val Gln Val Arg Asp Ala Glu Pro
                100                 105                 110

Gly Ala Asp Ala Glu Pro Gly Ala Asp Ala Glu Pro Gly Ala Asp Asp
            115                 120                 125

Ala Glu Glu Val Glu Gln Lys Gln Leu Gln Lys Arg Phe Gly Gly Phe
    130                 135                 140

Thr Gly Ala Arg Lys Ser Ala Arg Lys Leu Ala Asn Gln Lys Arg Phe
145                 150                 155                 160

Ser Glu Phe Met Arg Gln Tyr Leu Val Leu Ser Met Gln Ser Ser Gln
                165                 170                 175

Arg Arg Arg Thr Leu His Gln Asn Gly Asn Val
                180                 185

<210> SEQ ID NO 2
<211> LENGTH: 176
<212> TYPE: PRT
<213> ORGANISM: Homo sapiens

<400> SEQUENCE: 2

Met Lys Val Leu Leu Cys Asp Leu Leu Leu Leu Ser Leu Phe Ser Ser
1               5                   10                  15

Val Phe Ser Ser Cys Gln Arg Asp Cys Leu Thr Cys Gln Glu Lys Leu

-continued

```
                        20                  25                  30
His Pro Ala Leu Asp Ser Phe Asp Leu Glu Val Cys Ile Leu Glu Cys
        35                  40                  45

Glu Glu Lys Val Phe Pro Ser Pro Leu Trp Thr Pro Cys Thr Lys Val
    50                  55                  60

Met Ala Arg Ser Ser Trp Gln Leu Ser Pro Ala Ala Pro Glu His Val
65                  70                  75                      80

Ala Ala Ala Leu Tyr Gln Pro Arg Ala Ser Glu Met Gln His Leu Arg
                85                  90                  95

Arg Met Pro Arg Val Arg Ser Leu Phe Gln Glu Gln Glu Glu Pro Glu
            100                 105                 110

Pro Gly Met Glu Glu Ala Gly Glu Met Glu Gln Lys Gln Leu Gln Lys
        115                 120                 125

Arg Phe Gly Gly Phe Thr Gly Ala Arg Lys Ser Ala Arg Lys Leu Ala
    130                 135                 140

Asn Gln Lys Arg Phe Ser Glu Phe Met Arg Gln Tyr Leu Val Leu Ser
145                 150                 155                 160

Met Gln Ser Ser Gln Arg Arg Thr Leu His Gln Asn Gly Asn Val
                165                 170                 175
```

BIOPOLYMER SEQUENCE COMPARISON

CROSS-REFERENCE TO RELATED APPLICATIONS

This application claims priority to U.S. Provisional Application Ser. No. 60/250,743, filed on Dec. 1, 2000, which is incorporated by reference in its entirety.

BACKGROUND

The invention relates to comparing biopolymer sequences. Nucleic acids and proteins are two types of biopolymers that have complex sequences. Nucleic acids are polymers composed of a sequence of nucleotides. At a given position, one of four nucleotides can be present. One function of nucleic acids is to encode polypeptides.

Polypeptides are polymers composed of a sequence of amino acids. At a given position, one of twenty amino acids can be present. The sequence of amino acid in a polypeptide chain determines the structural fold that the polypeptide prefers to adopt. The properties of each amino acid side chain are unique and varied. Relevant properties for structure and function include hydrophobicity, size, charge, and rotamer preference.

For analysis, polymer chains are typically represented as a string of alphabetical characters, each character abbreviating the identity of a monomer in the chain. It is known to classify biopolymer sequences by their similarity to characterized sequences. Function is then imputed on the basis of the classification. For example, a sequence that is 70% identical to a protease and is 100% identical at residues demonstrated to mediate the enzymatic function of proteases is likely form a compound with protease activity.

Determining similarity for protein sequences is nontrivial for at least the following reasons. First, similar protein sequences can include insertions or deletions that shift the frame of comparison. Second, whereas two identical amino acids at a given position are clearly similar, measures of similarity of any two non-identical amino acids can fall within a large range. Further, the same pair of non-identical amino acids that function similarly in one context, may not in another context.

A variety of computer-based techniques have been developed to compare protein sequences. For example, the BLAST algorithm (Basic Local Alignment Search Technique; e.g., described by Altschul, et al. (1990) *J. Mol. Biol.* 215:403–10) allows for gaps of various sizes. A scoring scheme penalizes gaps, the enlargement of gaps, and non-identity. Further, a matrix that describes all possible pairs of amino acids at a given position is used to determine the extent of non-similarity at the position.

It is also possible to compare a biopolymer sequence to a profile of a family of similar sequences. This comparison can be made using an implementation of a Hidden Markov Model (HMM). Profile HMMs are a class of probabilistic models particularly adept for profile searches of biological sequences (Churchill (1989) *Bull. Math. Biol.* 51:79–94; Krogh et al. (1994) *J. Mol. Biol.* 235:1501–1531; Hughey and Krogh (1996) *Computer Applications in the Biosciences* 12:95–107; Eddy et al. (1995) *J. Comp. Biol.* 2:9–23; Durbin et al. (1998) *Biological Sequence Analysis: Probabilistic Models of Proteins and Nucleic Acids* Cambridge University Press; Gribskov et al. (1987) *Proc. Natl. Acad. Sci. USA* 84:4355–58). Profile HMMs include a network of nodes. Nodes are used to indicate the probability of a given monomer at a particular sequence position "emit" monomers at particular sequence positions. The probability depends on the frequency of the given monomer at the particular position in the family of similar sequences. Traversal of a path across the network of nodes of a profile HMM produces a single sequence that a likely family member.

SUMMARY

The invention provides, among other aspects, methods, software, and systems for comparing biopolymer sequences. The model includes at least two different characterizations of states of matching between segments of sequences at defined positions. Examples of states of matching include: similarity and dissimilarity between objects, as well as similarity to a reference, e.g., a reference sequence or a sequence profile.

In one aspect, the invention features a method that includes specifying a model of a set of biopolymer sequences, and comparing a given set of sequences to the model. The model indicates at least two different characterizations of states of matching between elements in at least two respective regions of the sequences. For example, the model includes a first module and second module that each characterizes a state of matching between elements in respective regions of the sequences such that the state of matching of the first module differs from the state of matching from the second module. Examples of states of matching include similarity between elements of different regions of the sequences, dissimilarity between elements of different regions of the sequences, and similarity to a reference (e.g., a sequence profile or a reference sequence). The method can be a machine-based method.

In some embodiments, one of the characterizations indicates a state of similarity and another of the characterizations indicates a state of dissimilarity. The state of similarity can be determined by a similarity scoring matrix, and the state of dissimilarity. can be determined by a dissimilarity scoring matrix. The dissimilarity scoring matrix can be a function of the similarity scoring matrix, e.g., it can be an arithmetic inverse of the similarity scoring matrix.

The set can include two or more sequences, e.g., at least three sequences. The biopolymer sequences are, for example, amino acid sequences or nucleic acid sequences.

The model can be a probabilistic model. For example, the model, such as a hidden Markov Model can express a probability that the given set of sequences is a set of sequences of the model. Each modules can include a network of nodes, and each node can represent a distribution of monomers (e.g., particular nucleotides or amino acids) at corresponding positions in the sequences of the set. The network may enable positioning of insertions or deletions between a sequence of the set and another sequence of the set, e.g., to offset the register of sequences of the set relative to each other.

The distributions of at least some of the nodes of each module can differ from each other. Likewise, the distributions of some other nodes can be the same. At least some of the distributions can be a function of a scoring matrix that relates occurrences of each monomer at a position in one of the sequences to occurrences of monomers at corresponding positions in at least another sequences. Another exemplary distribution is a function of the independent probability that a monomer occurs (e.g., in a genome, in a general database, or in a specific database). In another exemplary distribution, $P(a,b)$ of monomers $a$ and $b$, a scoring matrix $S(a,b)$, and independent probabilities of monomers, $Q(a)$ and $Q(b)$ are related such that $S(a,b)=\log(P(a,b)/(Q(a)\ Q(b)))$.

In some embodiments, the model further includes a third module that indicates the similarity or dissimilarity between a third region of each sequence of the set. The third module can indicate similarity between a third region of each sequence of the set and a sequence profile. The third region can be positioned between the first and second module or otherwise with respect to the sequence order. The sequence profile is indicated, for example, by altered scoring matrices. Examples of sequence profiles include profiles of a modification site, an active site, a regulatory site, a domain, and so forth. The modification site can be a processing site, e.g., a processing site that indicates a preference for at least a basic residue, e.g., a dibasic site. Examples of processing sites include convertase processing sites and secretase processing sites.

One of the modules of the model can be trained using a training set of sequences.

The sequences of the given set can include sequences from different species. Categories of species include, for example, eukaryotic, prokaryotic, archeal, plant, fingal, animal, vertebrate, invertebrate, and mammalian species. The sequences can be nucleic acid sequences (e.g., genomic nucleic acid, organellar nucleic acid, or transcribed nucleic acid). The sequences can include, e.g., non-coding regions, regulatory regions such as transcriptional or translational regulatory regions.

In another aspect, the invention features a method that includes: defining a sequential pattern of biopolymer sequence segments, the pattern comprising a similar segment and a dissimilar segment; comparing a first biopolymer sequence to a reference to identify similar and dissimilar segments in the first sequence; and determining if the similar and dissimilar segments of the first biopolymer sequence match the defined sequential pattern. The comparing and the determining can be concurrent. The method can be a machine-based method.

The reference can include a reference sequence and/or a sequence profile. The comparing and determining can be repeated for a plurality of sequences, e.g., such that multiple combinations of sequences selected from a plurality of sequences are compared.

The plurality of sequences can include sequences from different species of the same or different phyla. Each of the multiple combinations can include sequences from different species. The determining can include identifying a value evaluates the matching to the defined sequential pattern. The values can be used to rank the combinations. If the similar and dissimilar segments of the first biopolymer sequence match the defined sequential pattern, the biopolymer that includes one of the segments (e.g., the similar segment) of the first biopolymer sequence can be assayed, e.g., for expression or for an activity described herein.

In another aspect, the invention features a method that includes: evaluating sets to return a value and identifying sets which return values that exceed a threshold. Each set includes a first sequence from sequences of a first species and a second sequence from sequences of a second species. Additional sequences can be included in each set. The evaluating includes: (i) comparing the first and second sequence of each set to identify similar and dissimilar segments; and (ii) returning a value indicative of the match between the similar and dissimilar segments of the set and a defined pattern of similarity and dissimilarity. The method can be a machine-based method.

In yet another aspect, the invention features a method that includes: a) comparing a query sequence to each candidate sequence of a plurality of candidate sequences by a method that includes: i) identifying a first segment in the candidate sequence and a first segment in a query sequence; ii) determining the first measure that is a measure of the similarity between the first segments; and iii) determining a second measure that is a measure of the similarity between segments of the query sequence and the candidate sequence, the segments being other than the first segment; and b) identifying a selected candidate sequence from the plurality of candidate sequences, wherein a comparison of the first and second measures of the selected candidate sequence indicate at least a threshold extent of localized similarity. The method can be a machine-based method.

The invention also provides a method that includes: determining a first comparison score for a first region of a first and second sequence using a first set of scoring parameters; determining a second comparison score for a second region of the first and second sequence using a second set of scoring parameters, the second set differing from the first set; and determining an overall comparison score that is a function of the first and second comparison scores.

Further, the invention features a method that includes: receiving first and second sequences of elements; processing the sequences using a model that (i) defines ordered relationships between elements of the first and second sequences, and (ii) tunes the registers of the first and second sequences relative to the ordered relationship and each other; returning an evaluation indicating correspondence between the first and second sequences and the model. The registers indicate a relative positioning of the first and second sequences to allow staggering, gaps, insertions, etc.

In another aspect, the invention features a method of identifying a processed segment in a query amino acid sequence. The method includes: a) identifying a query segment in the query amino acid sequence; b) identifying candidate segments from a plurality of candidate sequences; c) identifying one or more candidate segments having substantial sequence homology to the query segment; d) aligning the query amino acid sequence to the one or more candidate amino acid sequences of the one or more candidate segments identified in c), such that the query segment is matched to the one or more identified candidate segments; e) determining a first similarity score between the matched query segments and the one or more identified candidate segments; f) determining a second similarity score between a region of the query amino sequence other than the query segment and one or more corresponding regions from the one or more candidate amino acid sequences; and g) comparing the first and second similarity scores, wherein the difference (or other function) of the first and second similarity scores is correlated with the likelihood that the query segment is a processed segment. The segments are flanked by a first and a second boundary. A boundary can be selected from the group consisting of: (1) a protein terminus, e.g., amino or carboxyl terminus, of the full-length protein (e.g., as translated); (2) a signal sequence; (3) an amino acid sequence motif or pattern; and (4) a processing site.

The method can further include determining if the difference between the first and second similarity scores is greater than a threshold parameter, e.g., a threshold parameter supplied by a user. The user can vary the threshold parameter in order to customize the sensitivity of the method. The query amino acid can be obtained from a first species and the plurality of candidate amino acids can be obtained from at least a second species, i.e., a different species from the first species. The plurality of candidate amino acids can be obtained from multiple species, e.g., 2, 3, 4, 5, 6 or more species.

The difference between the first and second similarity scores is computed by subtracting the second similarity score from the first similarity score or by dividing the first similarity score by the second similarity score.

The region other than the query segment can be a region amino terminal to the query segment, a region carboxy terminal to the query segment, or a region the entire polypeptide except the query segment.

The processing site can be identified by a processing site profile. In another embodiment, the processing site is identified by a Hidden Markov Model (HMM), e.g., a constrained topology HMM. Profiles and HMMs can incorporate preferences for sequences flanking the processing site and so forth. An HMM can be utilized to detect a signal sequence and processing sites, and to align the query and candidate amino acid sequences.

Examples of processing sites include a protease recognition site, e.g., a site recognized by a convertase (subtilisin; subtilisin-related proteases, PC 1/3, PC2, PACE4, PC4, PC5/6, and PC7/8; Kexin-like serine proteases; Furin; N-arginine dibasic convertase; a Kex2-related endoprotease) or secretase (e.g., α-, β-, or γ-secretase), e.g., a prohormone processing site. An exemplary processing site is a sequence that includes one or more basic residues. The method can identify more than one processed segment, e.g., two, three, four, five or more processed segments in a sequence. Tthe method can be executed in a computer system, e.g., using a computer-readable program code. A user can vary parameters and optional filters with each repetition in order to customize the sensitivity of the method. In addition, the method can further include procedures to verify that an identified segment is a processed segment. For example, the processed segment can be synthesized, e.g., in vitro using chemical synthesis, or in cells, e.g., using recombinant expression.

All patents and references cited herein are incorporated in their entirety by reference.

BRIEF DESCRIPTION OF THE DRAWINGS

FIG. 5 is a scoring matrix.
FIG. 6 is a sequence comparison.

DETAILED DESCRIPTION

A model is used to represent a relationship between positions in two or more structured data objects. The model (a so-called "constrained topology model") includes a topology that indicates different states of matching between elements in respective regions of the data objects.

Figure 1:
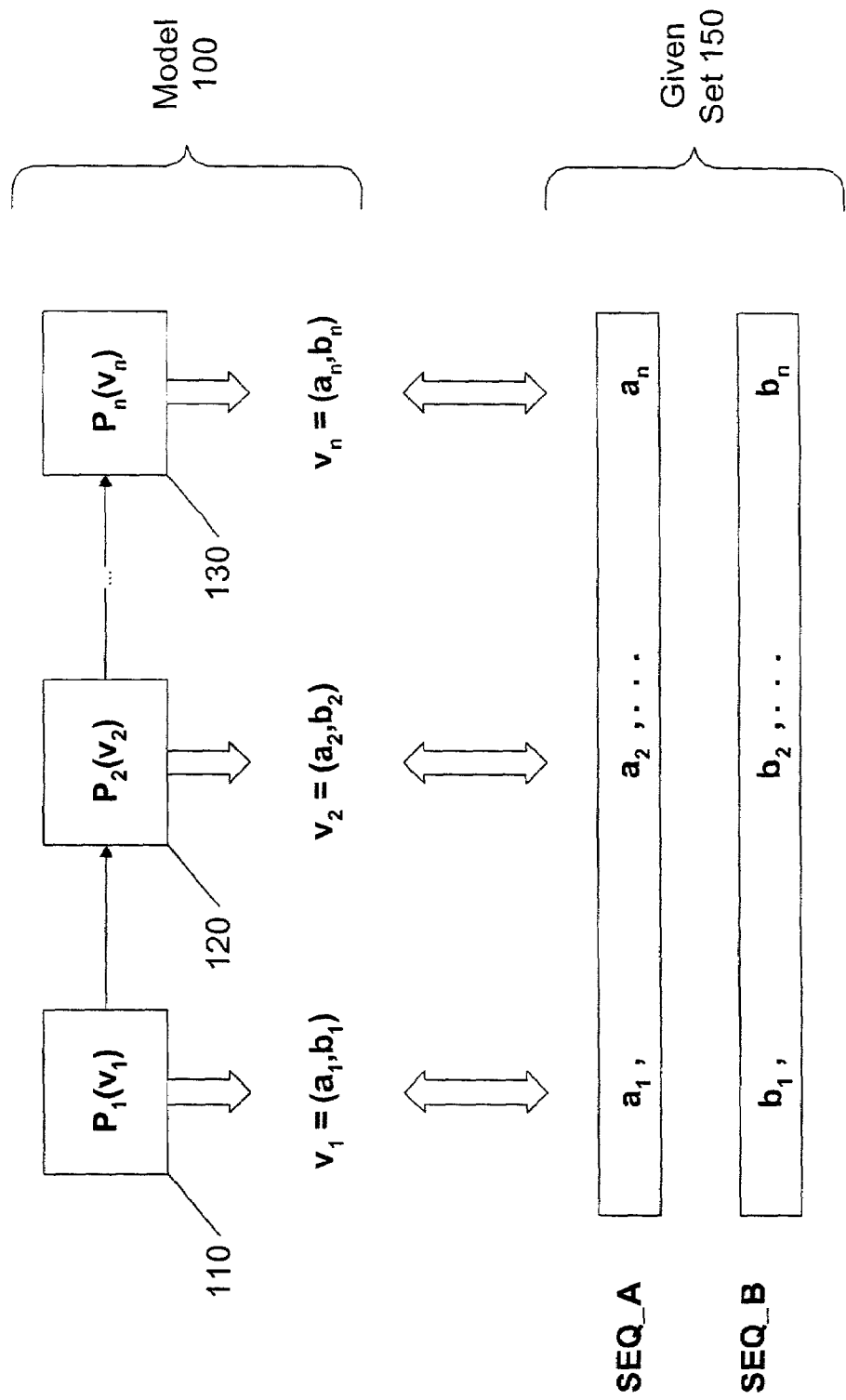
FIGS. 1, 3, 4, and 7 are block diagrams.

Referring to the example in FIG. 1, the model 100 includes nodes (110, 120, 130) that are linked in order. The model represents a set 150 of sequences, SEQ_A which includes $\{a_1, a_2, \ldots a_n\}$, and SEQ_B, which includes $\{b_1, b_2, \ldots b_n\}$. In this example, each node corresponds to a defined position in SEQ_A and SEQ_B. For example, node 110 corresponds to the first position which has the value $a_1$ in SEQ_A and $b_1$ in SEQ_B. Additional nodes can be present, for example, between node 120 and node 130 to represent elements between $a_2$ and $a_n$, and $b_2$ and $b_n$.

Each node represents a vector that is a set or ordered values, the first value referring to the corresponding element in SEQ_A and the second value referring to the corresponding element in SEQ_B. For example, node 110 represents the vector $v_1$ which is defined by $(a_1, b_1)$, i.e., the first value of SEQ_A, $a_1$, and the first value of SEQ_B, $b_1$.

Each node is programmed by a distribution of vectors P. The distribution varies from node to node, depending on the topology of the model 100. In the case of node 110, the distribution $P_1(v)$ indicates the likelihood that v is a particular vector. Where the elements at the first position of either sequence are selected from a finite set, it is trivial to enumerate the probability for each possible vector. The sum of the probabilities equals 1. Where the elements at the first position are selected from an infinite set, a mathematical function or algorithm can describe the probability for a vector. The integral of the function over the vector space equals 1.

The model 100 indicates different states of matching at different defined positions by using different distributions $P_1, P_2, \ldots P_n$. The distribution can be defined by a scoring scheme, e.g., a matrix that relates occurrences of an element in one object with occurrences in another.

Table 1 describes there hypothetical and exemplary distributions:

TABLE 1

| | Similarity | | | Profile Match | | | Dissimilarity | | |
|---|---|---|---|---|---|---|---|---|---|
| | A | B | C | A | B | C | A | B | C |
| A | .33 | 0 | 0 | 0 | 0 | 0 | 0 | .11 | .11 |
| B | 0 | .33 | 0 | 0 | 1 | 0 | .11 | 0 | .11 |
| C | 0 | 0 | .33 | 0 | 0 | 0 | .11 | .11 | 0 |

The three matrices, "similarity", "profile", and "dissimilarity", are three different match states between $a_n$ and $b_n$. The similarity matrix in Table 1 requires that $a_n$ and $b_n$ are identical. In a more complex distribution, the matrices might score ("A", "B") as similar with a reduced score relative to an exact match, but with a greater score than ("A", "C") or ("B", "C").

The dissimilarity matrix in Table 1 requires that $a_n$ and $b_n$ are non-identical. In a more complex distribution, different dissimilar pairs might be weighted differently.

The profile matrix in Table 1 requires that $a_n$ and $b_n$ be identical to a the value "B." A more complex profile matrix, might be weighted to prefer "B," but also accommodate "A" at a reduced frequency. In some cases, a profile matrix does not require matching between $a_n$ and $b_n$. For example, if the profile indicates a preference both A and B rather than C, the following might be true: P("A", "B")=P("A", "A"). In other cases, the profile may also indicate matching. An example here, if the profile indicates a preference both A and B rather than C, might be: P("A", "A")=P("B", "B")>P("A", "B")=P("B", "A").

A spectrum of matrices consisting of matrices that vary between the examples illustrated in Table 1 represents a range of different matching states. Any possible matrix may be used to indicate a particular state of matching, e.g., a matrix that is in the spectrum or a matrix outside of the spectrum.

Figure 2:
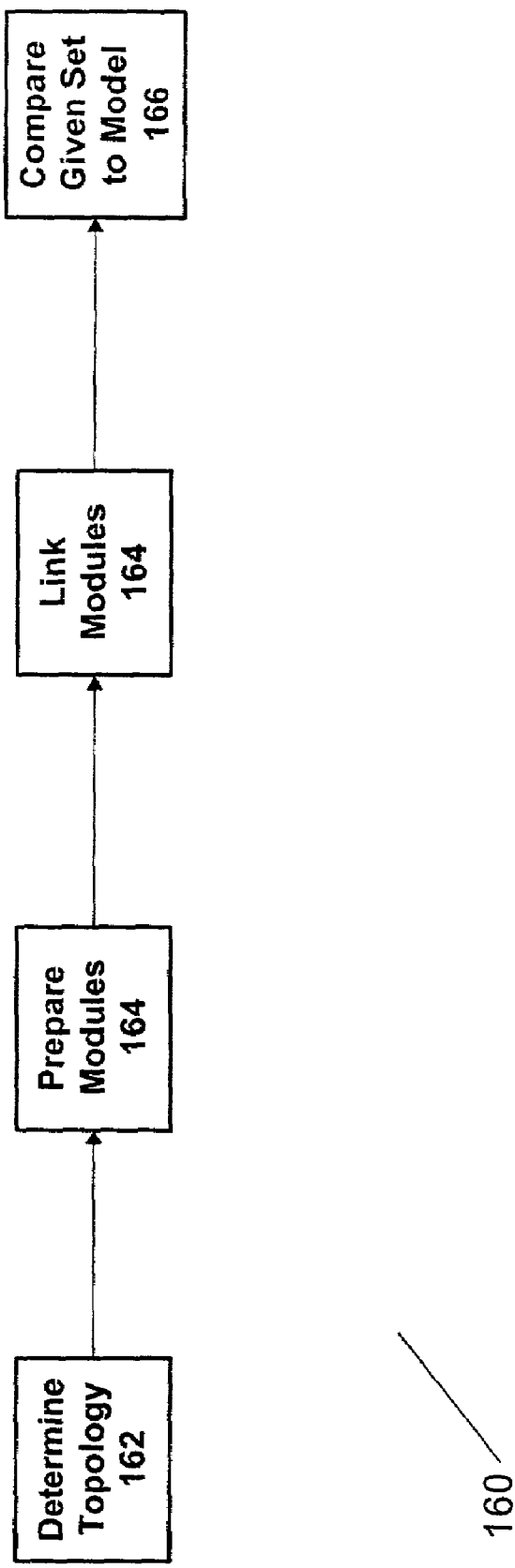
FIG. 2 is a flow chart.

Referring to FIG. 2, a model can be constructed and used according to the exemplary process 160. The process includes: determining 162 a topology of different match states, then preparing 164 modules of nodes for each match state, and linking 166 the modules to form the model. Once the model is in place, a given set 150 of structured data objects can be compared 168 to the model.

A module, which can include one or more nodes, is a unit that can conveniently be prepared in isolation from other modules. Preparing a module, for example, can include either specifically programming nodes, training the nodes, or a combination of the two. Training involves providing the modules with data objects that are intended to be within the representation of the module. The distributions of nodes in the module are then tuned, e.g., in an iterative process, until the module encompasses the training set of data objects.

Referring again to the exemplary process 160, the modular nature of the model facilitates varying the order of blocks 162, 164 and 166. For example, the modules can first be prepared 164, then a topology determined 162, and then modules linked 166. In another example, untrained (e.g., "naïve") modules are first linked 166, and then prepared 164 by training against a set of sequences. In this method, the training process itself reveals the topology that is determined 162 from the training set of sequences.

Referring again to the example in FIG. 1, the comparing can include determining the overall likelihood that a given set of sequences 150 is represented by the model. In one implementation, the overall likelihood, Sc, that SEQ_A and SEQ_B are represented by the model is:

$$Sc(\text{SEQ\_A}, \text{SEQ\_B}) = \prod_{k=1}^{n} P_k(a_k, b_k) \quad (1)$$

This value is also an example of a score.

The match Hidden Markov Model (mHMM or "integrated HMM") is one implementation of the above model. The mHMM uses aspects of Hidden Markov Models (described below) to represent the different states of matching. The mHMM is used, for example, to identify members of a family of biopolymer sequences that are characterized by a topological pattern of regions of similarity and dissimilarity. Similarity is indicative of conservation during the course of evolution, whereas dissimilarity is indicative of divergence. In many cases, sequence determinants of function and structure are conserved. This implementation is described in detail below.

Preprohormones 180 are a class of proteins that are processed in cells to form hormones 188. Hormones function to stimulate receptors and regulate physiological processes (additional description of biological aspects is provided below). The sequence of hormones is highly conserved. In contrast, not all regions of a preprohormone are conserved. Preprohormones have a characteristic organization that set forth in FIG. 3. Within the preprohormone sequence, the sequence of a hormone is flanked by processing sites 186, 190 which are recognized by processing enzymes, typically proteases such as convertases. However, other regions 184, 192 of the preprohormone, e.g., upstream and downstream of the hormone processing sites 186, 190, are typically divergent in sequence. An additional feature of preprohornones is an N-terminal signal sequence 182 that directs secretion of hormones from cells.

Figure 4:
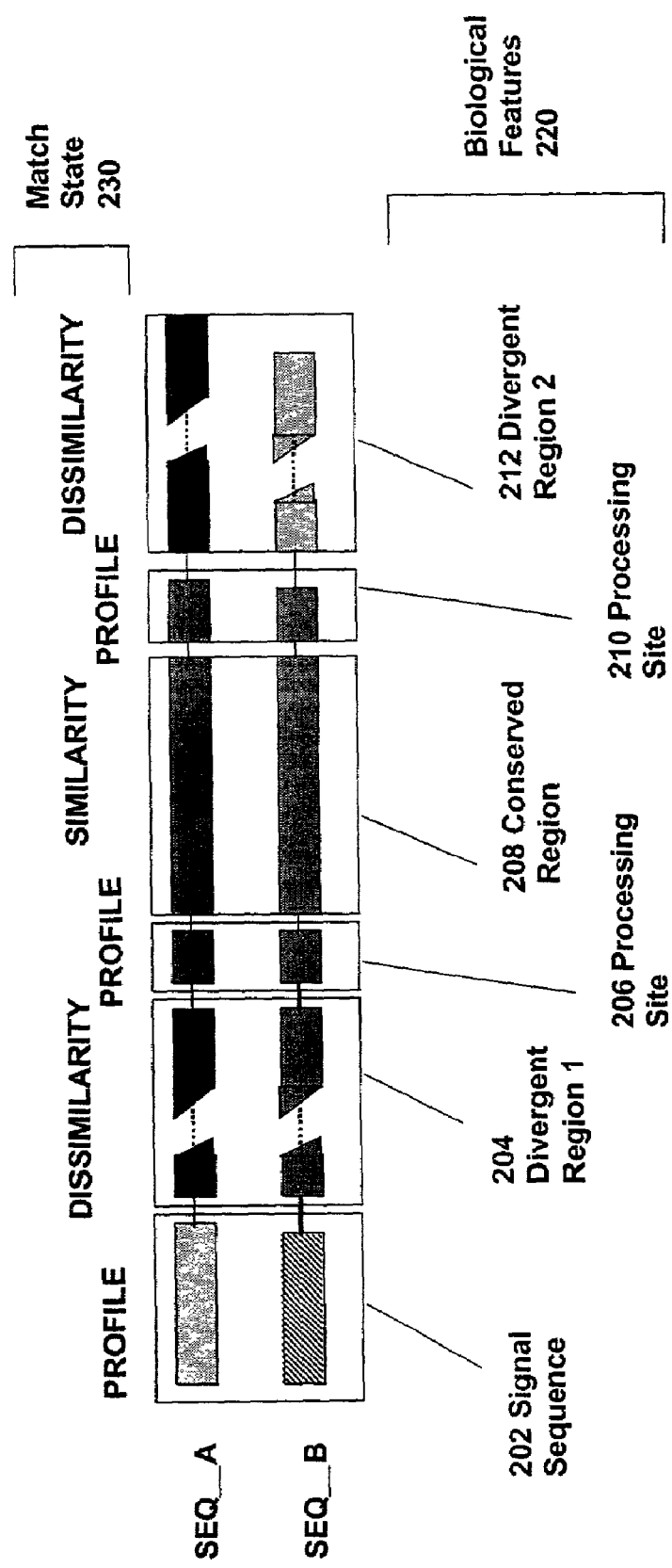

Referring to FIG. 4, an mHMM 200 is constructed to represent the likelihood that a pair of amino acid sequences are related preprohornones.

Modules that represent respective regions of a set of biopolymer sequences are linked to represent the topology of a prohonnone. The modules are linked in an order (from left to right) that corresponds to the organization of biological features 220. These features 220, from N-terminus (left) to the C-terminus (right), include: a signal sequence 202, a first divergent region 204, a processing site 206, a conserved region 208 that is the hormone, a processing site 210, and a divergent region 212. As shown, each module represents a different characterization of the match state 230. In the case of the signal sequence 202 and processing site 206, 210 modules, the match states require matching to a profile. In the case of the conserved region 208, the match state requires similarity between SEQ_A and SEQ_B. In the case of the divergent regions 204, 212, the match state requires dissimilarity between SEQ_A and SEQ_B.

The profiles for signal sequences and processing sites model the conformance of sequence segments in both SEQ_A and SEQ_B to profiles that represent preferred amino acids for preprohormone features. For example, signal sequences are typically hydrophobic (e.g., aliphatic amino acids such as leucine, isoleucine, and methionine). Nielsen et al. (1999) *Protein Engineering* 12:3–9 have trained profile HMMs to model signal sequences. These trained profile HMMs, which model just one sequence, are adapted to produce a model of a pair of sequences which fit the profile for a signal sequence. The state space of an mHMM is the Cartesian product of the two HMM spaces, each of which is a profile HMM for a single sequence. In some cases, the mHMM is actually determined by taking the Cartesian product of two HMMs. In these cases, the mHMM can be modified, e.g., by pruning nodes that are redundant or non-essential, e.g., unreachable.

The module 206, 210 for processing sites are modified profile modules that are trained on known hormone processing sites, and recognize one or more basic residues (i.e., arginine (Arg) and lysine (Lys)). In some versions of the model, the processing site profile includes a preference for a dibasic sequence (e.g., "Arg-Arg" "Arg-Lys" "Lys-Arg" and "Lys-Lys").

In contrast to these profile modules, the hormone region 208, which is conserved biologically, is represented by a module 208 that searches for a similarity match state. Likewise, the divergent regions 204, 212 flanking the processing sites are modeled as dissimilarity match states. In this implementation, the similarity and dissimilarity match states are both specified by distributions that relate to a scoring matrix for amino acids.

A typical amino acid scoring matrix is a matrix of 20×20 elements. Each matrix element provides a score based on the frequency of an amino acid pair aligning in a conserved region relative to their occurrence at random. A number of scoring matrices are commonly used for the pairwise matching of amino acid sequences. These include: the PAM and BLOSUM matrices (Henikoff and Henikoff (1992) *Proc. Natl. Acad. Sci. USA* 89:10915–10919; Dayhoff M. O. et al, (1978) A model of evolutionary change in proteins. In Dayhoff M. O. ed., *Atlas of Protein Sequence and Structure*, volume 5, supplement 3. National Biomedical Research Foundation, Washington, D.C., pp. 345–352.). FIG. 5 illustrates an exemplary BLOSUM matrix.

For the nodes that model similarity match states in the conserved region 208, the distribution P(a,b) is related to the BLOSUM scoring matrix S(a,b) by equation 2:

$$S(a, b) = \log\left(\frac{P(a, b)}{Q(a) \cdot Q(b)}\right) \qquad (2)$$

where $Q_a$ and $Q_b$ are the independent probabilities that a or b occur.

For nodes that model dissimilarity match states, e.g., in the divergent regions 204 and 212, the distribution P(a,b) is related to the scoring matrix S'(a,b) by equation 3:

$$S'(a, b) = \log\left(\frac{Q(a) \cdot Q(b)}{P(a, b)}\right) = -S(a, b) \quad (3)$$

S'(a,b) is a function of the inverse of S(a,b), as shown above. Nodes within any of the above modules for the different match states of a preprohormone sequence are interconnected with each other and with additional nodes that model deletions or insertions in one sequence with respective to the other sequence. Each connection can be associated with a transition probability. When the connection is a transition from a match state to an insertion state, the transition probability represents the likelihood that the model can accommodate a gap in the alignment between the two sequences. For example, in the module that models a similarity match state, the transition probability to reach a node that allows an insertion or deletion can be low relative to other modules.

After the designing of the modules for the different match states of a preprohormone sequence, the modules are linked together according to the preprohormone structural organization to form an overall model that can identify preprohormones.

Once formed, the model is used to evaluate a pair of amino acid sequences. Because of its probabilistic nature and because of the nodes that allow for insertions and deletions, the model can concurrently align the two amino acid sequence and fit the match states of the two amino acid sequences to the topology model of preprohormones. The model can output an overall score that represents the likelihood that the two sequences are preprohormones.

To discover new preprohormones from a protein or nucleic acid sequence, the model can be applied in a pairwise analysis of the sequences of two different species. Pairwise combinations of sequences, one from a first database of sequences from a first species and the other from a second database of sequences from a second species, are analyzed by the model. A score is determined for each pair. The pairs can ranked, and high scoring pairs outputted. Alternatively, pairs that score above a threshold value can be outputted. A related example of the use of the model is provided below in Example (below).

The model described above identifies new hormones by comparing the extent of similarity in different segments of protein sequences to identify sequences that have the organization of preprohormones. Of course, the model can also use nucleic acid sequences to identify new hormones. Nucleic acid sequences are directly related to amino acid sequence by the codon table. Due to the degeneracy of the codon table, nucleic acid sequences contain additional information about evolutionary relationships that can aid the matching process. The model can be adapted to include nodes and transitions that allow for untranslated nucleic acid sequences, such as introns, to be accommodated by the matching process.

Models for topologies of match states can be applied widely within the field of bioinformatics.

For example, a pattern of similarity and dissimilarity can be based on the three-dimensional structure of an initial protein. Segments (of one or more amino acids) of similarity and of divergence can be patterned based on the three-dimensional topology of the structure. In particular, positions on the surface of the protein are designated as segments of divergence, whereas positions on the interior of the protein are designated as segments of similarity. This design conforms with experimental observations that the interior of proteins is constrained by geometry. However, substitutions can occur within the interior. Often these are compensated by substitutions at other interior positions. A model that searches for patterns of similarity at interior positions would identify subsets of proteins that diverge from the initial protein, but whose interior positions are conserved among sequences of the subset relative to surface positions.

In another example, the pattern is used to identify sites on nucleic acids that are bound by regulatory proteins. Because of their functional importance, these sites are frequently conserved, whereas surrounding nucleic acid sequence can diverge. The helical nature of double-stranded B-form DNA results in the major groove rotating about the helical axis every 10 base pairs. Often proteins are bound on one face of the DNA helix, and likewise recognize specific bases that are spaced about 10 basepairs apart. For example, if a protein complex recognizes a three basepair site in one major groove and four basepair site in an adjacent major groove, the center-to-center distance of these two sites can be about ten base pairs apart such that seven basepairs are intervening. A topology model to identify sites that have this structural conformation might include the following regions: a first non-conserved region; a first conserved region of three nucleotides; a second non-conserved region of seven nucleotides and first conserved region of four nucleotides. Related examples include prokaryotic and eukaryotic promoter structures, DNA replication origins, and translational and mRNA stability regulatory regions on RNA.

In still other examples, the pattern includes modules that define repeats. Each node of the module can point to more than one sequence segment. Thus, for two repeats, each node can point to defined positions in both repeats within each sequence of the set being modeled.

Similarly, in another example, the model can include a node that defines the distributions of monomers at defined positions at two positions within each sequence of the set being modeled. This can be useful for modeling positions that interact, e.g., sequences that covary during evolution so that a mutation in one position results in a compensatory position in at another position. Covarying positions can occur, for example, at protein-protein interfaces and within the core of a protein.

Models for topologies of match states can also, of course, be applied widely to the comparison of data objects.

For example, human speech (or other sounds) can be recorded as a sequence representing the sound waves. An mHMM is used to determine if two sequences of speech are related. In one implementation, a model is used to identify the accent or language training of an individual by comparing the speech of an test individual to a reference individual. For a particular accent, the model predicts that the pronunciation or intonation of certain words differs from the speech of the reference individual and that other words are similar to the reference individual. Such models are trained to detect geographic origins of individuals based on speech. Similarly, the models can also be trained to detect emotion as speech patterns of highly emotive speech differ from regular speech by have predictable differences in some segments while maintaining similarity in other segments.

In another example, an mHMM is used to compare visual images which are stored as structured two-dimensional datasets. The model searches for pairs of images among a database of images for a pair that are similar in one region, but that differ in another. For example, the model can be designed to compare complex images such as reconnaissance photographs, scientific imaging (e.g., X-rays, Magnetic Resonance Image (MRI), microscopic images), facial images, and so forth. For example, in the case of an MRI image, elements of the model programmed to match identify landmark organs and features, whereas elements programmed to differ identify pathological features, such as a tumor, inflammation, or necrosis.

Of course, this implementation can also be used for three-dimensional datasets (e.g., MRI scans of patients, topographic satellite images, or reconstructed three-dimensional images) and four-dimensional datasets (e.g., three-dimensional data captured at more than one time interval).

In still other examples, patterns of characteristic match states are used to identify relationships, e.g., relationships in financial data, economic data, ecological data, meterological data, astronomical data, failure analysis, engineering data (including data relating to architecture, chemical engineering, and materials), chemical data, and physics data.

The invention can be implemented in digital electronic circuitry, or in computer hardware, firmware, software, or in combinations thereof Apparatus of the invention can be implemented in a computer program product tangibly embodied in a machine-readable storage device for execution by a programmable processor; and method actions can be performed by a programmable processor executing a program of instructions to perform functions of the invention by operating on input data and generating output. The invention can be implemented advantageously in one or more computer programs that are executable on a programmable system including at least one programmable processor coupled to receive data and instructions from, and to transmit data and instructions to, a data storage system, at least one input device, and at least one output device. Each computer program can be implemented in a high-level procedural or object oriented programming language, or in assembly or machine language if desired; and in any case, the language can be a compiled or interpreted language. Suitable processors include, by way of example, both general and special purpose microprocessors. Generally, a processor receives instructions and data from a read-only memory and/or a random access memory. Generally, a computer can include one or more mass storage devices for storing data files; such devices include magnetic disks, such as internal hard disks and removable disks; magneto-optical disks; and optical disks. Storage devices suitable for tangibly embodying computer program instructions and data include all forms of non-volatile memory, including, by way of example, semiconductor memory devices, such as EPROM, EEPROM, and flash memory devices; magnetic disks such as, internal hard disks and removable disks; magneto-optical disks; and CD_ROM disks. Any of the foregoing can be supplemented by, or incorporated in, ASICs (application-specific integrated circuits).

Figure 7:
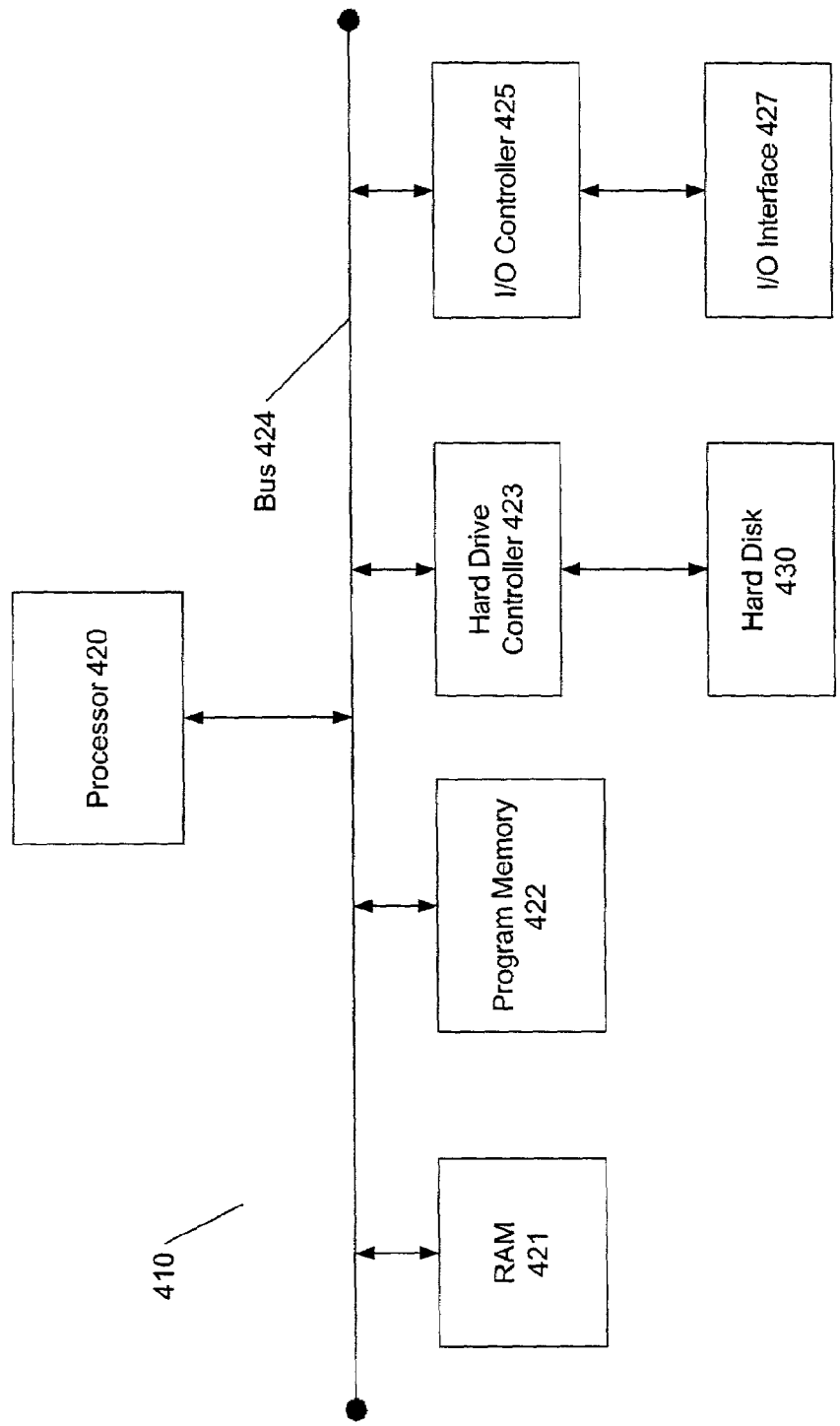

An example of one such type of computer is shown in FIG. 7, which shows a block diagram of a programmable processing system (system) 410 suitable for implementing or performing the apparatus or methods of the invention. The system 410 includes a processor 420, a random access memory (RAM) 421, a program memory 422 (for example, a writable read-only memory (ROM) such as a flash ROM), a hard drive controller 423, and an input/output (I/O) controller 424 coupled by a processor (CPU) bus 425. The system 410 can be preprogrammed, in ROM, for example, or it can be programmed (and reprogrammed) by loading a program from another source (for example, from a floppy disk, a CD-ROM, or another computer).

The hard drive controller 423 is coupled to a hard disk 430 suitable for storing executable computer programs, including programs embodying the present invention, and data including storage. The I/O controller 424 is coupled by means of an I/O bus 426 to an I/O interface 427. The I/O interface 427 receives and transmits data in analog or digital form over communication links such as a serial link, local area network, wireless link, and parallel link.

One non-limiting example of an execution environment includes computers running Windows NT 4.0 (Microsoft) or better or Solaris 2.6 or better (Sun Microsystems) operating systems. Browsers can be Microsoft Internet Explorer version 4.0 or greater or Netscape Navigator or Communicator version 4.0 or greater. Other environments could, of course, be used.

Hidden Markov Models

HMMs are a class of probabilistic models particularly adept for profile searches of biological sequences (Churchill (1989) *Bull. Math. Biol.* 51:79–94; Krogh et al. (1994) *J. Mol. Biol.* 235:1501–1531; Hughey and Krogh (1996) *Computer Applications in the Biosciences* 12:95–107; Eddy et al. (1995) *J. Comp. Biol.* 2:9–23; Durbin et al. (1998) *Biological Sequence Analysis: Probabilistic Models of Proteins and Nucleic Acids* Cambridge University Press; Gribskov et al (1987) *Proc. Natl. Acad. Sci. USA* 84:4355–58). HMMs have a linear sequence of inter-connected nodes. The sequence of nodes is initiated with a begin state (B) and terminates with an end state (E). Nodes can include nodes for a match to the model, nodes for insertions, and nodes for deletions. The probability of advancing from one node to another is governed by a transition probability. Each node also has an associated emission probability that represents a constraint on the identity of an amino acid at a given position in a sequence. The node "emits" an amino acid depending on that state that it is in. Thus, the emission probabilities represent the tolerance of the model for an amino acid to emitting an amino acid within the constraint (Match State) or differing from the constraint.

A query sequence can be compared to an HMM to measure the probability that the query sequence is a member of the HMM, i.e., a member of the model. A variety of methods can be used to compute the probability of a sequence being a member of an HMM. The Viterbi algorithm, which is routine in the art, is used to identify the most probable path in the HMM for a given polypeptide sequence. Then probability of that polypeptide sequence occurring the model is computed by multiplying all the probabilities along that path. Alternatively, the forward-backward algorithm (Durbin et al. (1998) *Biological Sequence Analysis: Probabilistic Models of Proteins and Nucleic Acids* Cambridge University Press) may also be used to directly compute the probability that the sequence was generated by the HMM involved.

Figure 3:
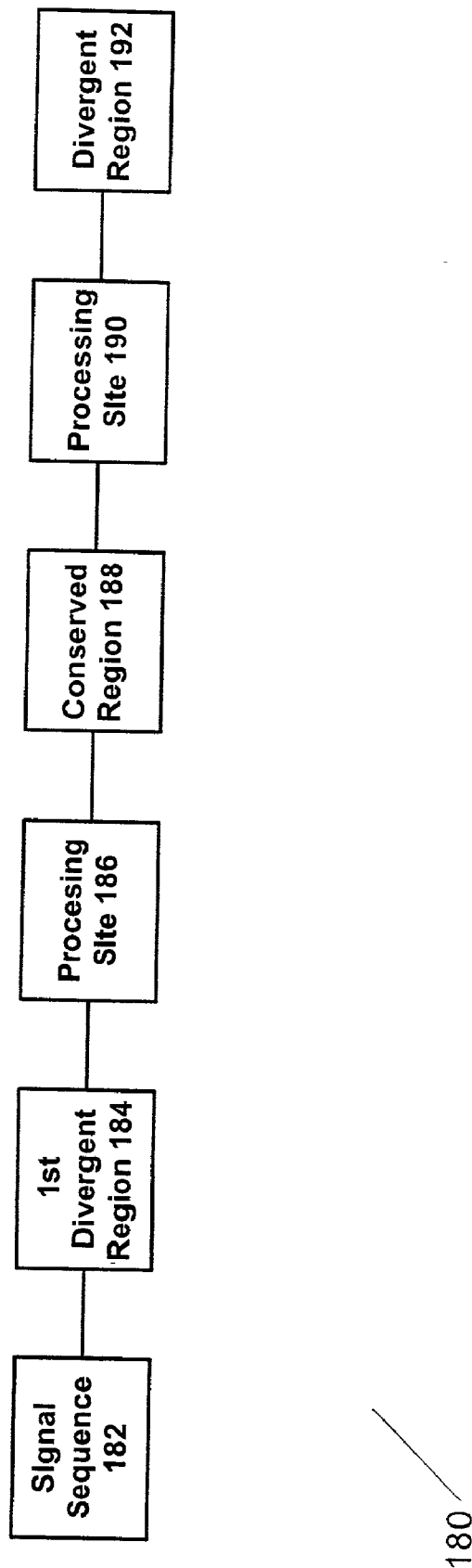

Hidden Markov models have successfully been used in inferring general phylogeny probabilistically from protein sequences. The current invention uses HMMs to model a segment of an amino acid sequence that is well-preserved (i.e. well conserved) in a first and second species due to biological function in comparison with surrounding amino acid sequences in the same polypeptide. The underlying concept is phylogenetic: the two sequences from the first and second species are hypothesized to have evolved from a common ancestor, an estimate is made of how well-preserved a putative processed segment 188 is in comparison with its surroundings 184,192, which have diverged disproportionately (FIG. 3). For example, the processed segment can be a polypeptide hormone that is constrained by evolution to bind and activate a receptor, whereas the surrounding sequences, e.g., the remainder of the prohormone may have no biologic functional constraint.

The following features are contemplated: (1) alignment of homologous sequences (e.g., human and rodent) with an integrated heterogeneous HMM that models well-preserved and divergent subsequences separately as well as, e.g., enforcing marker constraints (e.g., to a profile such as a double basic residue) and signal sequence; (2) differential phylogenetic scoring of the HMM alignment by using explicit models of nucleotide substitution to generate separate divergence estimates for the well-preserved putative hormone coding sequence and the surrounding divergent preprohormone sequence.

In one Implementation, the Following Computational Steps are Executed:

1. Providing a database of protein sequences from a first species (e.g., human) and a database of protein sequences from a second species (e.g., mouse).
2. Filtering out protein sequences without signal sequences or a processing site.
3. Pairwise alignment of sequences from the first database to sequences from the second database with an integrated HMM that models the signal sequence, sequence markers, and both the divergent and well-preserved regions.
4. Computing the expected number of amino acid and/or nucleotide substitutions (e.g., based on the codon of the relevant amino acids) in the putative preprohormone, $K_p$, and in the putative hormone sections, $K_h$, as marked by the integrated HMM alignment (heterogeneous phylogeny). Several phylogenetic models can be used for this statistic (Miyata, et al. (1980) *J. Mol. Evol.* 16:23–36; (Li (1997) *Molecular Evolution* Sinauer Associates).
5. Ranking of the alignments by the $\Delta K = K_h - K_p$ statistic.
6. Evaluation of the alignments in the search interface with various search parameters and thresholds.

The order of a number of steps can be changed. For example, sequences can be pairwise aligned first (step 3), and then filtered for signal sequences (step 2). Also additional steps can be added, e.g., filtering sequences for a length requirement such that the sequence fits in a range between a minimum length and a maximum length. Such optional steps and various parameters can be added by a user, e.g., by interaction with a user interface capable of receiving selections and parameters.

Protein Sequence Model

The overall organization of a putative hormone coding sequence in a preprohormone is shown in FIG. 3. Enclosed by markers is an evolutionary well-preserved region due to its highly specialized function, which is also marked by a signal sequence. This formation resides in a region that has diverged in sequence similarity between the species (human and rodent) depending on how apart they are in the phylogenetic tree. One main statistic is the measure of relative preservation in the hormone sequence as compared with its genomic vicinity. The evolutionary nucleotide substitution models from phylogenetics can be applied heterogeneously to the well-preserved and divergent segments of the sequence.

Integrated Hidden Markov Model

Hidden Markov models are a convenient probabilistic framework in which to pose the matching problem. A novel topology is used to enforce sequence marker constraints and the simultaneous prediction of the signal sequence. Also, once sequences are matched by maximizing likelihood, a phylogenetic score is computed using a 2- or 4-parameter model, that ranks the matched sequences according to the relative slow evolution of the hormone coding sequence compared with that of the surrounding preprohormone sequence. In the following, topologies of the HMM modules and the overall HMM are presented. The well-preserved region is modeled by a pairwise matching HMM with PAM or BLOSUM based output matrices. The signal sequence module is a specialized HMM that was developed in Nielsen et al. (1999) *Protein Engineering* 12:3–9. The double basic markers are matched amino acid nodes with output matrices that require the alignment to contain the double basic pairs.

The overall alignment of the combined HMM is carried out with the Viterbi algorithm as is routine in the art.

A Novel Method of Hormone Discovery

Peptide hormones form a large class of first messenger molecules that activate cell surface receptors. Although the cell surface receptors typically have a characteristic primary and tertiary protein structure, peptide hormones do not. Consequently, it can be a challenge to identify them on the basis of their amino acid sequence.

Peptide Hormone Receptors. Peptide hormones activate receptors on the cell surface, or in endocytic vesicles. Peptide hormone receptors typically have at least one transmembrane spanning domain, an extracellular domain for binding the peptide hormone, and an intracellular domain for transducing signals. The intracellular signals can activate pathways that include cytoplasmic signaling proteins and second messengers molecules.

Many hormone receptors also include a domain that mediates receptor oligomerization. In some cases, the hormone binding domain itself mediates oligomerization. Binding of the hormone to the domain results in dimerization or further oligomerization of the receptor. Oligomerization then drives intracellular signaling.

Non-limiting examples of peptide hormone receptors include the insulin receptor, insulin-like receptors, human growth hormone receptor, and GPRCs (see below).

G Protein Coupled Receptors (GPCRs). GPCRs form a large gene family that includes receptors for peptide hormones. According to the GPCR Data Base (available online described in Horn et al. (1998) *Nucleic Acids Res.* 26:277–281 and Horn et al. (2001) *Nucleic Acids Res.* 29:346–349) there are more than 22 peptide receptors classes, including at least 69 known receptors. In additions, there may be numerous orphan receptors that fit into this class. Because of the commonality of seven membrane spanning α-helices, and several conserved amino acids, identification of a putative GPCR from DNA or protein sequence is straightforward.

Because of their extracellular sites of action and upstream position in signaling pathways, GPCRs are frequent targets for drug development. Because of their characteristic structure, putative GPCRs can be identified relatively easily, e.g., by the presence of seven transmembrane spans and some conserved amino acid residues. Numerous GPCRs have be identified on this basis from sequence information. However, for many of these, the ligand that activates the receptor is unknown. Thus, these receptors are termed "orphan" receptors. The ligands for these receptors may be small molecules, lipids, peptides, or proteins.

Peptide hormones are polymers of amino acids ranging from 3 to approximately 70 residues. They are synthesized as larger proteins (a preprohormone), secreted and processed. Each has a signal sequence that is necessary for the transport of the protein across the lipid bilayer into the endoplasmic reticulum, and into secretory vesicles for processing and secretion. Here the signal sequence is removed resulting in the prohormone. Within the secretory vesicle further processing takes place, e.g., the polypeptide can be digested by processing enzymes or specific endopeptidases. In general, hormones are surrounded by a pair of double basic residues, i.e. Arg-Arg, Arg-Lys, Lys-Arg, or Lys-Lys is found directly adjacent to the putative hormone. These double basic residues are recognition sites for processing enzymes, e.g., serine proteases, that cleave the prohormone to liberate the active peptide. One other common feature of peptide hormones is the presence of one or more blocking group on the carboxy or amino terminals. An amidated carboxy terminal can be found in perhaps half of the peptide hormones, while a pyroglutamate representing the first amino acid can found in a small portion of peptide hormones. These blocking groups act to make the peptide resistant to amino or carboxy peptidases, and thus increase the circulating half life of the hormone.

Even with these common biological properties, the identification of a peptide hormone from a DNA or protein sequence is exceedingly difficult. Whereas all GPCRs are closely related at the DNA or protein sequence level, generally peptide hormones that bind to the receptors do not have highly conserved features that are readily detected. However, within discrete families of prohormones, sequence conservation is detectable. For instance there are four members of opioid-like peptides. These prohormones, proopiomelanocortin (POMC), proenkephalin, prodynorphin, and pronociceptin (proN/OFQ), share similar genomic structures, and a very slight similarity of gene sequence, most notably the Y(F)GGF of enkephalin, β-endorphin, dynorphin and N/OFQ. However, it is important to note that even within this gene family, a conventional sequence search of GenBank for similar sequences to proenkephalin does not retrieve all three of the other members of the family. Conventional search strategies are unsuccessful in identifying novel peptide hormones, especially those that do not belong to known peptide hormone families.

Many peptide hormones have been identified by biochemical methods. Substance P was discovered based upon physiological actions of brain extracts. Met- and leu-enkephalin were discovered using a known receptor in a bioassay. Hughes and Kosterlitz isolated these two peptides from bovine brain using a smooth muscle bioassay and demonstrated binding of these two peptides to opiate receptors (Hughes and Kosterlitz *Nature* (1975) 258:577–80). It was several years later when these two peptides were found to be generated from a single prohormone. Mutt et al. used a chemical assay to identify carboxy-terminal amidated peptides, and in this way discovered NPY and peptide YY (see, e.g., Tatemato et al. (1982) *Nature* 296:659–60). Meunier et al. purified and sequenced N/OFQ from rat brain membranes (Meunier et al. (1995) *Nature* 377:532–5). CHO cells were transfected with ORL1, an orphan receptor. Ligands were identified based on the assumption that the endogenous ligand would inhibit cAMP accumulation as do the endogenous ligands for μ, δ, and κ-opioid receptors, the other receptors in that family. Orexin/hypocretin was purified from bovine brain by its ability to activate one of a panel of orphan receptors expressed in mammalian cells The discovery of each of these peptides has advanced the understanding of human physiology.

Peptide Hormones and Their Receptors. Peptide hormones are polymers of amino acids ranging from 3 to approximately 70 residues. They are synthesized as larger proteins, termed preprohormones that are secreted and processed. Each has a signal sequence that directs the transport of the protein across the lipid bilayer into the endoplasmic reticulum, and into secretory vesicles for processing and secretion. Within the endoplasmic reticulum, signal sequences are removed by signal peptidases resulting in prohormones. Within the secretory vesicle, or in the extracellular environment, further processing takes place. For example, the polypeptide can be digested by a processing enzyme such a specific endopeptidase (e.g., a convertase, subtilisin, Kexin-like serine protease, Furin, N-arginine dibasic convertase, or a Kex2-related endoprotease) (Brakch et al. (2000) *FEBS*267:626; Chesneau et al. (1994) *Biochemie* 76:234–240). The processing event cleaves the prohormone to release active hormone.

The hormone is then able to bind to cell surface receptors. For exocrine signals, the cell surface receptor is on another cell, e.g., a cell of another tissue. For autocrine signals, the cell surface receptor can be on the same cell as the secreting cell. Non-limiting examples of such cell surface receptors include the insulin receptor, insulin-like receptors, human growth hormone receptor, chemokine receptors (e.g., CCR family members), and G protein coupled receptors (GPRCs).

In addition to peptide hormones, other peptides can also be processed by cleavage at specific processing sites. For example, the Aβ peptide that is associated with Alzheimer's disease, is processed from APP by secretases, e.g., α-secretase and β-secretase, or α-secretase and γ-secretase. Erroneous processing by γ-secretase can result in amyloid formation. Furthermore, proviral proteins are also processed by a protease, e.g., HIVgp160.

The invention features, in part, a method for identifying new hormones by comparing the extent of similarity in different segments of protein and gene sequences. The method can identify pairs of sequences that are similar in one segment, but that differ in another segment. This topological pattern of similarity is, in one view, a model for sequence conservation in the similar segment and sequence divergence in the different segment. The topological pattern is constructed to capture either the observed or inferred structure of preprohormones.

Because a large number of preprohormones have been shown to contain more than a single hormone, the preprohormone sequences are scrutinized carefully in the hope of identifying additional hormones. This can be accomplished because of the rules that were discussed above. Hormones are frequently distinguished by double basic residues, although sometimes they begin after the signal sequence or end at the end of the protein. Unfortunately, double basic residues are common in all proteins, and one can not use this tag alone to detect hormones. One other crucial property suggests the likely presence of a hormone. Hormones are usually well conserved among species, while the intervening sequences of prohormones are not well conserved. The intervening sequences may not have a biological function.

This key property for the discovery of novel hormones is illustrated in the comparison of mouse and human preproN/OFQ depicted in FIG. 6. The 17 amino acid peptide N/OFQ is totally conserved among all species tested. In mouse and human proN/OFQ, the final 28 amino acids, separated by the sequence Lys-Arg, are also highly conserved in comparison to the remainder of the prohormone. This peptide, named OFQ2, has been shown to have binding affinity to a novel receptor, and possess analgesic activity. Thus, a second bioactive peptide resides within the same prohormone as N/OFQ. In contrast, the variable portion of the remainder of the prohormone is inferred to not contain biologically active hormones. In the case of proN/OFQ, there is evidence for an additional active compound, called nocistatin that is conserved between human and mouse, but not flanked by dibasic processing sites (Okuda-Ashitaka et al. (1998) *Nature* 392:286–9).

The invention provides a method for identifying peptide hormones from recently or soon to be available DNA and gene sequences despite their small size, and the apparent sequence diversity of these proteins. Parameters for the method can include: ranges for protein size (prohormones are small proteins), requirement for the presence of a signal sequence, and most importantly profiles or patterns defining a boundary sequence which is biological processing site. Peptide segments are defined as sequences which are flanked on both ends by one or two of a boundary sequence, the N-tenninus, and/or the C-terminus. One simple boundary sequence for identifying peptide hormones is a dipeptide consisting of two basic residues—arginine (Arg) and lysine (Lys). In this example, 'Arg-Arg' 'Arg-Lys,' 'Lys-Arg,' and 'Lys-Lys' are all acceptable boundary sequences. The peptide hormone can also begin after the signal sequence. Therefore, the signal sequence is also a contemplated boundary sequence. The method includes algorithms to compare the variability of sequence segments, when comparing human with other mammalian gene or protein sequences.

In addition other types of processed secreted proteins can be identified by this method. The boundary function is simply changed to reflect the specificity of the processing enzyme, e.g., protease.

For example, the boundary function can be altered to detect the recognition site of a secretase, e.g., α-, β-, or γ-secretase. The 4 kDa amyloid peptide, Aβ is produced by the proteolytic processing of a large transmembrane protein, β-amyloid precursor protein (APP). For example, β-secretase processes APP to yield an intermediate in Aβ production. The exact processing site of β-secretase starts with aspartic acid in APP. The transmembrane aspartic protease, BACE1, has been identified as the polypeptide component of β-secretase activity (Vassar et al. (1999) *Science* 286: 735). Results from mutagenesis and biochemical studies to understand the specificity of this protease are used to generate a profile for the β-secretase processing site. The profile is entered into the computer systems and/or executable code of the invention to search protein databases for novel amyloid proteins and/or secretase substrates.

Identification of Processed Segments

The method involves detecting boundaries which are processing sites with a polypeptide sequence. In addition, the carboxy terminus of the polypeptide sequence can serve as a boundary. The method can be implemented on a variety of scales. For example, it can be used to identify a processed segment in a single polypeptide sequence for which there is a related sequence from another species. Alternatively, the method can be used to identify a processed segment in a single polyp eptide sequence by comparison to a database of polypeptide sequences is provided, e.g., available polypeptide sequence translated from ESTs or genomic sequence from one more other species. The method can be also used to identify multiple processed segments from a database of sequences from a first species by comparison to a database of sequence from a second species, or multiple other species. Nucleic acid sequences can also be utilized (as described below).

Protein sequences are downloaded from GenBank (available from the National Center for Biotechnology Information, National Institutes of Health, Bethesda Md.), TrEMBL, and/or other sources. Alternatively, protein sequences can be obtained by translating nucleic acid sequence, e.g., a cDNA sequence or a genomic sequence. Gene-finding programs, e.g., GRAIL (Uberbacher and Mural (1991) *Proc. Natl. Acad. Sci. USA* 88:11261), and Genefinder (Solovyev et al. (1994) *Nucl Acids Res* 22:5156–5163), can be used to identify protein sequences from genomic sequence. Expressed sequence tag (EST) data can be translated in every reading frame to provide the protein sequence input for the search described above.

String searches are utilized to identify regions of protein that show similarity of sequence within double basic residues, but significant differences outside of the segment demarcated by double basic residues when comparing human versus mouse or other mammalian proteins. The "double basic residues" or "dibasic" motif consists of two or more lysine or arginine amino acids in a row. These are marker sequences for possible ends of hormones. Preferentially, one can look for amino acid sequences bounded by ends of the potential preprohormone or by double basic residues. In addition, one can look for such sequences with a glycine just before the final double basic residue. This process can be accomplished very rapidly using automata-based string-searching techniques such as the Boyer-Moore fast string searching algorithm.

In one implementation, the computer algorithm features a method of assessing varying rates of evolution in different segments of the sequence in an HMM framework. The algorithm can identify more than one homolog of the query protein, and compare the relative rate of evolution for each segment, e.g., the degree of sequence conservation, the constraints on sequence divergence.

Another next step which can be carried out before, during, or after the above step, is to find analogous, e.g., homologous proteins. The next step is to compare for the extent of similarity in the regions bounded by double basic residues or ends of the protein, between the query protein and its homolog. The next step, which can be carried out before, during, or after the previous step, is to compare similarities in the regions outside this set of double basic residues to the similarity of the region between the double basic residues.

If the region between the double basic residues is significantly more similar, continue, otherwise, reject the candidate hormone. This step can be implemented efficiently using automata-based methods for string search and string comparison, or can be implemented by sorting strings, and/or comparing by grey-code-like distance vectors. The similarity tests can also incorporate a cost function that counts preferred protein mutations less than non-preferred protein mutations, e.g., the BLOSUM and PAM matrices (available from the National Center for Biotechnology Information, National Institutes of Health, Bethesda Md.). For example, proteins Lys and Arg (Lysine and Arginine) are more interchangeable than Lys and Gly (Lysine and Glycine). Thus one can penalize strings which differ from Arg to Gly more than strings which differ by only Lys to Arg. Another step, which can be accomplished at various points, is selecting protein strings that have signal sequences at their N-terminus. If all the above tests match, the potential preprohormone can be evaluated using other methods.

In another embodiment, the method is performed, e.g., using a computer system, by executing the following steps:
1. Providing a first database of protein sequences from a first species (e.g., human) and a second database of protein sequences from a second species (e.g., mouse).
2. Optionally filtering out protein sequences from both databases based on various parameters (e.g., a size range) or criteria (e.g., presence of a signal sequence). Preferably, sequences which lack a processing site altogether are eliminated;
3. Identifying query segments in each database, wherein the query segments are between a first amino terminal boundary which is a processing site, and a second carboxy terminal boundary which is either a processing site or the carboxy terminus of the protein sequence.
4. Forming pairs of query segments by finding a related query segment from the pool of query segments identified in step 3 from the second database for each query segment identified in step 3 from the first database. This comparison step can be implemented in a variety of ways, e.g., using a string search, a FASTA, BLAST, or HMM search. The comparison can be evaluated to find the best related query segment. Possible scorings methods for the evaluation include % identity, PAM matrix scoring, BLOSUM matrix scoring, or probabilistic scoring, e.g., by computing the probability of the best path through an HMM. A user interface can be provided to allow the user to customize and/or optimizing the comparison step.
5. For each pair of query segment, aligning the complete polypeptide sequence from the first and second database such that the query segments are aligned as in the comparison step (step 4).
6. Computation of at least two statistics for the pair of aligned sequences (as aligned in step 5). The first statistic represents the similarity of the query segment region (i.e. the potential query segment region). The second statistic represents the similarity in a region outside the query segment region, e.g., amino and/or carboxy terminal to query segment. Alternatively, a statistic for the overall similarity of the pair can be used as the second statistic. The statistics can be a comparison score, e.g., % identity, PAM matrix scoring, BLOSUM matrix scoring, or probabilistic scoring, or a score based on a model for phylogenetic evolution (see below).
7. The first and second statistics are then compared in order to determine if the query segment is more conserved than the remainder of the protein. For example, if % identity is used for determining similarity in step 6, the comparison entails subtracting the % identity for the region outside the query segments from the % identity of the potential query segments. A positive difference is correlated with the query segment being an actual processed segment.
8. Query segments which are correlated with being processed segments are displayed or otherwise indicated. Optionally, a threshold parameter, e.g., provided by a user through a user-interface, can be used to tune the results. For example, the threshold parameter can be used to eliminate pairs that have a positive difference between the first and second statistics smaller than the threshold parameter.

The user can execute the above steps in a computer system repeatedly. For example, the user can initially utilize with a first set of parameters and optional filters which yield very few or now predicted processed segments. The user can then repeat the process by incrementally varying the parameters or the usage of filters to increase the number of predicted processed segments. Moreover, the user can monitor the results to determine if known processed segments are predicted. The user can continue this process until the number of predicted processed segments exceeds a criteria, e.g., an upper limit, or a number wherein all known processed segments are identified.

The method can also be modified to compare sequences from multiple species of organisms, or even all available sequences. Various clustering algorithms, e.g., hierarchical clustering, can be used to group query segments obtained from different species. Likewise, scoring statistics are available that can measure similarity for a multiple alignment or profile of grouped query segments.

Computer Algorithms

The software to compare human and non-human sequences and identify processing sites and potential pre-prohormones pairs can implemented with a variety of computational strategies. The software can utilize automata-based methods for string search and string comparison (e.g., the Boyer-Moore fast string searching algorithm), procedures for sorting strings, comparison employing grey-code-like distance vectors to search strings, Hidden Markov Models (HMM), and variations of HMM, e.g., "topology constrained HMM".

A variety of methods can be used for comparing two sequences and to obtain similarity scores. These methods include percent identity, the GAP program in the GCG® software package (available from Accelrys, San Diego Calif.), BLAST, and probabilistic measures obtained from HMMs, e.g., those described above.

To determine the percent identity of two amino acid sequences, or of two nucleic acid sequences, the sequences are aligned for optimal comparison purposes (e.g., gaps can be introduced in one or both of a first and a second amino acid or nucleic acid sequence for optimal alignment and non-homologous sequences can be disregarded for comparison purposes). In a preferred embodiment, the length of a reference sequence aligned for comparison purposes is at least 30%, preferably at least 40%, more preferably at least 50%, even more preferably at least 60%, and even more preferably at least 70%, 80%, 90%, 100% of the length of the reference sequence. The amino acid residues or nucleotides at corresponding amino acid positions or nucleotide positions are then compared. When a position in the first sequence is occupied by the same amino acid residue or nucleotide as the corresponding position in the second sequence, then the molecules are identical at that position (as used herein amino acid or nucleic acid "identity" is equivalent to amino acid or nucleic acid "homology"). The percent identity between the two sequences is a function of the number of identical positions shared by the sequences, taking into account the number of gaps, and the length of each gap, which need to be introduced for optimal alignment of the two sequences.

The comparison of sequences and determination of percent identity between two sequences can be accomplished using a mathematical algorithm. In a preferred embodiment, the percent identity between two amino acid sequences is determined using the Needleman and Wunsch (*J. Mol. Biol.* (48):444–453 (1970)) algorithm which has been incorporated into the GAP program in the GCG® software package (available from Accelrys, San Diego Calif.), using either a Blossum 62 matrix or a PAM250 matrix, and a gap weight of 16, 14, 12, 10, 8, 6, or 4 and a length weight of 1, 2, 3, 4, 5, or 6. In yet another preferred embodiment, the percent identity between two nucleotide sequences is determined using the GAP program in the GCG® software package, using a NWSgapdna.CMP matrix and a gap weight of 40, 50, 60, 70, or 80 and a length weight of 1, 2, 3, 4, 5, or 6. A particularly preferred set of parameters (and the one that should be used if the practitioner is uncertain about what parameters should be applied to determine if a molecule is within a sequence identity or homology limitation of the invention) are a Blossum 62 scoring matrix with a gap penalty of 12, a gap extend penalty of 4, and a frameshift gap penalty of 5.

The percent identity between two amino acid or nucleotide sequences can be determined using the algorithm of E. Meyers and W. Miller ((1989) *CABIOS* 4:11–17) which has been incorporated into the ALIGN program (version 2.0), using a PAM120 weight residue table, a gap length penalty of 12 and a gap penalty of 4.

The nucleic acid and protein sequences can also be compared using the NBLAST and XBLAST programs (version 2.0) of Altschul, et al. (1990) *J. Mol. Biol.* 215:403–10. BLAST nucleotide searches can be performed with the NBLAST program, score=100, wordlength=12 to obtain nucleotide sequences homologous to a query nucleic acid sequence. BLAST protein searches can be performed with the XBLAST program, score=50, wordlength=3 to obtain amino acid sequences homologous to query amino acid sequence. To obtain gapped alignments for comparison purposes, Gapped BLAST can be utilized as described in Altschul et al. (1997) *Nucleic Acids Res.* 25:3389–3402. When utilizing BLAST and Gapped BLAST programs, the default parameters of the respective programs (e.g., XBLAST and NBLAST) can be used. See on-line resources of the National Center for Biotechnology Information, National Institutes of Health, Bethesda, Md.

Phylogeny Based Scoring

Various techniques for estimating the number of substitutions between protein-coding sequences in phylogeny studies in order that they be used to serve as a distance between sequences in forming phylogenetic trees. In order to use these methods to generate sensitive measures of divergence, the actual codon sequences (i.e., nucleic acid sequences) from which the amino acid sequences were translated are compared to each other. In most of these methods, synonymous and nonsynonymous substitutions are treated separately. The end result is an estimate of number of substitutions per synonymous and nonsynonymous sites. Comparison of two homologous sequences (e.g., human and rodent) uses the HMM-identified locations of deletions and insertions that may have occurred after their divergence from a common ancestor. Two separate parameters are computed: $K_h$ for the putative hormone coding region and $K_p$ the preprohormone in which it is enclosed. This statistic $\Delta K = K_h - K_p$ provides a measure of the relative preservation of the functional region in the preprohormone and is used to rank matching sequences.

Development of an Homologous Aligned Sequence Viewer

The computer system can include a user interface to accept user selections, and user-defined parameters, as well as to display results.

The display of results can indicate one or more of the following: the presence and/or position of a signal sequence; the gene/protein identifier and species of the sequence containing an identified processed segment, and aligned sequences; the score for the processed segment region, the score for the region outside the processed segment, and the comparison statistic for the two scores; and the amino acid sequence of the identified processed segment and/or a complete alignment of the pair or group of sequence aligned in the comparison process. Colors and graphics can be used enhance the display and to highlight important features, e.g., the processed segment, and processing sites.

The user selections can include the following:

Species. The user can select a database of sequence from a variety of organismal species, e.g., human, mouse, rat, cow, *Fugu, Drosophila, Brachydanio rerio, C. elegans*, etc.

Signal Sequence. The user can determine if sequences are filtered for the presence of a signal sequence.

Processing Site. The user can elect the type of processing site to utilize, e.g., double basic, double basic followed by glycine, a convertase recognition site, a secretase recognition site, a protease recognition site, and so forth. The user can specify if the carboxy terminus of the polypeptide can also be used as a boundary for a processed segment.

Minimum and Maximum Sequence Length. The user can specify the minimum and/or maximum length of the complete polypeptide sequences.

Minimum and Maximum Segment Length. The user can specify the maximum length of the query segments.

Sequence Length Difference Ratio. The user can specify the maximum difference in the lengths of the complete polypeptide sequences.

DB-Region Length Difference Ratio. The user can specify the maximum difference in the lengths of the query segments.

DB-Region-Center Same Ratio. The user can specify the minimum scores of match (depending on the metric used, i.e. % identity, PAM score or HMM match score) of the query segments.

DB-Region-Sides Difference Ratio. The user can specify the maximum scores of match (depending on the metric used, i.e. % identity, PAM score or HMM match score) of the windows (the divergent sequence) around the double-basic query segments.

DB-Region-Sides Window Ratio. The user can specify the sizes of the windows (divergent sequence) around the double-basic query segments as a percentage of the query segment length in number of amino acids.

DB-Region Start Difference Ratio. The user can specify the maximum difference in the number of amino acids the double-basic query sequences can be offset from the start of the complete polypeptide sequences.

Verification of Hormone Sequences

Sequences predicted to include a hormone sequence can be subjected to further analysis to verify the predictions. For example, mRNA analysis can be used to determine if and where the mRNA encoding the hormone is expressed in cells of an organism. Antibodies can be used to determine if the hormone peptide or polypeptide itself is detectable present in biological samples.

Expression Pattern. The existence of an appropriate mRNA transcript is confirmed by Northern analysis and/or reverse transcriptase PCR (rtPCR) using RNA isolated from a panel of tissues, e.g., such as a panel include brain, heart, skeletal and smooth muscle of the animal from which it was identified.

Once a preprohormone is predicted by the method described above, the presence of the appropriate MRNA transcript encoding the preprohormone is verified. Primers are synthesized based upon the gene sequence of the predicted hormone. rtPCR is conducted using the primers. Primers are designed based upon the sequence from the animal paired with the human sequence for each particular putative hormone. The primer can span an intron if possible so that genomic DNA does not interfere with the experiment. rtPCR is conducted on mRNA extracted from a variety of tissues, e.g., including brain, heart, kidney, liver and skeletal and smooth muscle. If transcripts are found in more than one tissue, mRNA levels can be compared by quantitative PCR. Because the rtPCR analysis is relatively quick and inexpensive, it is conducted for each putative hormone identified.

Northern analysis is carried out using standard methods. Briefly, RNA, isolated as described above, is dried and suspended in RNA loading buffer containing formamide (50%), formaldehyde (2.2 M), glycerol and MOPS buffer. The RNA sample is run in a 1% agarose gel, stained with ethidium bromide, soaked in NaOH/NaCl, sodium citrate buffer (SSC), transferred by gravity onto Nytran membranes (Schleicher & Schuell, Keen, N.H.), and cross linked onto the membrane. The transfer is checked under UV light.

For hybridization, the RNA filter is placed in a hybridization tube with prehybridization solution containing formamide, SDS, Denhardt's solution, salmon sperm DNA and SSC buffer. The filter is prehybridized for at least 4 h at 42° C. The gel fragment (in low melting agarose) is melted at 70° C. for 5 min and added to T7 primer and M13 reverse primer. This mixture is boiled for 5 min and slowly cooled on the lab bench. To this mixture [$^{32}$P]-dCTP and 2 µl of Klenow fragment is added to label the probe complementary to the RNA of interest. The labelled probe is purified using a spin column. Approximately $5 \times 10^6$ counts are used for the hybridization, which is conducted overnight at 42° C. The filter is washed in SSC containing 0.1% SDS at an appropriate temperature (e.g., approximately 55° C.). The bands hybridizing to probe are visualized using Kodak X-OMAT film by exposure at −80° C. as required, and/or visualized and quantitated using a Storm 840 PhosphorImager (Molecular Dynamics). Filters can be stripped for future use by boiling in 0.1% SDS.

In Situ Hybridization. The discrete and heterogeneous localization of its mRNA is a prerequisite for characterization of an endogenous compound as a neurotransmitter or hormone. Moreover, the localization also provides considerable insight into the actions of endogenous compounds, particularly for neurohormones. Accordingly, in situ hybridization is conducted on all putative hormones found by rtPCR to have significant levels in whole mouse or rat brain.

In situ hybridization is performed by the method described in Waleh et al., (1995) *Cancer Res.* 55:6222–6226, see also, Wilcox et al. (1988) *J. Clin. Invest.* 82:1134–1143. Sections 20 µm thick are prepared from freshly dissected rat or mouse brain. Sections are fixed in 4% formaldehyde for 10 min, then washed in 0.5× SSC and treated with proteinase K (5 µg/ml) for 10 min at room temperature. Prehybridization is performed in 50% formamide, 0.2 M NaCl, 20 mM Tris (pH 8.0), 5 mM EDTA, 1× Denhardt's solution, 10% dextran sulfate, and 10 mM DTT, at 55° C. for 3 h. [$^{35}$S]-labeled riboprobes (sense and antisense) are prepared by using the Riboprobe Gemini System II (Promega, Madison, Wis.). Labeled probes ($1 \times 10^6$ cpm per section) are added and incubated at 55° C. overnight. Sections are washed with 2× SSC, 10 mM β-mercaptoethanol (β-ME), and 1 mM EDTA, and then treated with 20 mg/ml RNase A for 30 min at room temperature. This procedure is followed by a high stringency wash for 2 h in 0.1× SSC, 10 mM β-ME, 1 mM EDTA, at 55° C. and two more washes with 0.5× SSC. Sections are dehydrated with ethanol, vacuum dried, and subjected to autoradiography.

Antibodies. Antibodies to the proposed peptide hormone are generated and utilized to precipitate, isolate and sequence the hypothetical hormone. Antibodies can be generated by commercial suppliers using routine methods from a peptide synthesized based upon the proposed hormone sequence. The antibodies are used to purify the peptide hormone from tissue sources found to have high levels of the prohormone mRNA, and presumably of the peptide of interest. The peptide-antibody complex is precipitated with a secondary antibody and the hormone released by low pH. Reverse phase HPLC is used to isolate a fraction with identical elution profile as the synthetic peptide. The sequence is optionally verified by microsequencing.

Characterization of Confirmed Hormones.

Once it has been confirmed that the processed peptide exists in situ, the peptide is synthesized and labeled with either tritium or $^{125}$I. The ability of the synthetic peptide to bind to receptors on the cell surface of the tissues found to have significant amount of the transcript or the hormone is determined. Binding is characterized with respect to $K_d$ and $B_{max}$ in various tissues. For peptides expressed in the brain, a general in vivo profile is determined by studying effects on locomotion, balance, respiration, etc. subsequent to intracerebroventricular (ICV) injection.

Synthesis. Small peptides, e.g., peptides about 5 to 60 amino acids in length, are produced by peptide synthesis using routine methods. Consideration is given to peptides with disulfide bonds, and the possibility of aberrant folding, or incorrect processing or modification since a synthetic peptide is not produced in the natural context of the prohormone.

Bioassays. A purified or synthesized peptide is applied to cell, e.g., a cell expressing an orphan receptor, e.g., an orphan GPCR. Signalling of the receptor is monitored to determine if the identified peptide hormone activates the receptor. For example, tissue culture cells are transfected with an expression vector for the GPCR prior to the assay. In a high-throughput platform, all known GPCR identified in a genome are cloned into expression vectors and individually transfected into host cells. The host cells are grown in microtitre plates. Mayer et al. ((1999) *Science.* 286:971–4) describe high density plates and methods for screening for signaling events on such plates. The peptide hormone identified by the invention is applied to the plates in order to screen for its ability to activate all known GPCR to thereby identify the receptor for the peptide hormone.

A purified or synthesized peptide can also be administered to a subject animal, e.g., a non-human mammal. The physiological effects of the local or systemic administration are assessed.

Receptor Binding. Once it has been confirmed that the processed peptide exists in situ, the peptide is synthesized and labeled with tritium, $^{35}$S, or $^{125}$I. If the peptide has a tyrosine residue, it is labeled with $^{125}$I. The advantage of a radioiodinated peptide is higher specific activity leading to a far more sensitive binding assay. In the absence of a tyrosine, the peptide is synthesized with one tritium residue using precursors so labelled. Peptide hormone binding to cells is assayed in the tissues found to have significant amount of the transcript or the hormone.

Binding assays are conducted, e.g., as described for opiate receptor or ORL1 binding (Meunier et al. (1995) *Nature* 377:532–5). For example, assays are performed with a 1 ml incubation containing the radiolabeled peptide, brain or other tissue, with or without 1–10 μM of the unlabeled peptide to define non-specific binding. Samples are incubated to equilibrium (usually 1–2 h) then filtered over glass fiber using a Brandel or Wallac harvester. Binding is optimized by varying temperature of incubation, tissue concentration, and concentration of the radiolabeled peptide. Binding is characterized with respect to $K_d$ and $B_{max}$ by conducting saturation isotherms in various tissues.

Biochip Assays. Also contemplated are methods to assay the state of gene expression in a cell after application of a hormone identified by the method described herein. The identified hormone is applied to the cell, and mRNA is harvested at various time intervals after application. The mRNA is converted to labeled cDNA and hybridized to gene chips containing probes to a large number of expressed genes. Changes in the amount of hybridization to each probes reflects changes in gene expression following application of the hormone. Such methods are routine to the skilled artisan. The results of such experiments provide functional information about the mode of hormone action.

EXAMPLE

Search of Swiss-Prot

The string search methodology was used to search available databases for polypeptide hormones using the mHMM model. Swiss-Prot is a database of known protein sequences. It was searched using the search paradigm described herein. Table 2 lists 44 prohormones identified using the described search method. These 44 represent a large proportion of the 51 prohormones known in this database. In addition to these 44 known prohormones, the string search paradigm identified 33 additional proteins, listed in Table 3. It is interesting to note that of these 33 additional proteins many are other signaling proteins (see left column) such as cytokines and growth factors. Possibly, these cytokines evolved from prohormones into functional molecules for which processing is no longer required. Alternatively, these molecules may actually be processed in a manner similar to the prohormones, but that the processing activities and processed forms have not been identified. Hence, this methodology can also be applied to identify these types of hormones.

TABLE 2

Known Hormones Identified in SwissProt

| | |
|---|---|
| ACTH | motilin |
| Adrenalmedulin (ADM) | MSH |
| Agouti-Related Peptides | Neuromedin U |
| Amylin | Neurotensin |
| ANP | Neurturin |
| Apelin | NPY (Neuropeptide Y) |
| Calcitonin | Nociceptin |
| CCK | Orexins |
| CGRP | Oxytocin |
| CNP (C-Type Naturetic Factor) | PACAP (Pit. Adenylate Cyclase Activating Pp.) |
| Cortistatin | PPY (Pancreatic Hormone) |
| Corticotropin Releasing Factor (CRF) | PHI (Same precursor with VIP) |
| Dynorphin | Prolactin-Releasing Peptide (PrRP) |
| b-Endorphin | Parathyroid hormone (PTH) |
| Endothelin 1 | PTH-RP (Parathyroid Releasing Hormone) |
| Endothelin 2 | Peptide YY (PYY) |
| Endothelin 3 | Somatostatin |
| Enkephalin | Substance P |
| Galanin | Substance K (Neurokinin A) |
| Gastrin | TRH |
| Gastrin Releasing Peptide (GRP) | Vasopressin |
| Glucagon | VIP |
| GRF (Growth Hormone Releasing Factor) | TEGT (testis enhanced gene transcript) |
| LHRH1 | PSP94 (Prostate secretory protein) |
| MCH (Melanin Concentrating Hormone) | |

TABLE 3

Other Polypeptides

| | |
|---|---|
| FGF-3, 5, 7, 10, 17, 18 | MAGF (Microfibril Associated Protein) |
| GDNF | MINK (K-Channel) |
| Neurturin | K-Channel related peptide |
| CD8, 28 | L-Type Ca2+ Channel, gamma subunit |
| PDGF-2 | Myelin Po Protein |
| TGF | Dif-2 (Differentiation dependent immed. early) |
| VEGF | Eosinophil |
| HBNF-1 (Heparin Binding Neurite Outgrowth Factor) | Syntaxin 1B (vesicle docking) |
| | Syntaxin 2 |
| MIP (Macrophage Inflamatory Protein) | TMP21 (Vesicle trafficing protein) |
| NGF | Coagulation Factor III |
| Cytokine A21 | PGD2 synthase |
| Interferon alpha | Syndecans |
| IGF Binding Protein 1B, 2, 3 | FKBP12 (FK506 binding protein) |

TABLE 3-continued

| Other Polypeptides | |
|---|---|
| IL7 | Folate receptor |
| | ERp29 |
| | COMT |
| | Connexin 32 |
| | Cytostatin |

In another implementation, parameters can be altered in order to minimize the number of false positives, and to increase the number of true positives. Additional databases can be used to provide the input protein sequence. For example, EST sequences from a public or private EST database, e.g., human, mouse, and rat ESTs, can be translated in all reading frames.

Other embodiments are within the following claims.

What is claimed:

1. A method for determining a probablity that a set of biopolymer sequences is a member of a hidden Markov model (HMM) of a set of known biopolymer sequences comprising the steps of:
   a) constructing said HMM by
   1) identifying at least two regions in the set of known biopolymer sequences and determining a state of matching for each region using scoring matrices, wherein at least one state of matching is similarity and at least one state of matching is dissimilarity:
   2) producing modules for each of said match states from one or more nodes linked in order, wherein each node represents a distribution of monomers at corresponding positions in the sequences of said set of known biopolymer sequence;
   3) linking said modules in the order in which regions occur to form the HMM;
   b) comparing a second set of biopolymer sequences to said HMM by evaluating the scoring matrices for the second set of biopolymer sequences to produce an output score that is the probability that the second set of biopolymer sequences is member of the HMM; and
   c) outputting said score.

2. The method of claim 1, wherein said determining said state of matching comprises determining said state of matching against a reference sequence.

3. The method of claim 1, wherein one of said scoring matrices is an arithmetic inverse function of another one of said scoring matrices.

4. The method of claim 1, wherein safe set of known biopolymer sequences comprises sequences from different species.

5. The method of claim 4 whereby said different species comprises mammalian species.

6. The method of claim 1, wherein said set of known biopolymer sequences consists of two sequences.

7. The method of claim 1, wherein said set of known biopolymer sequences comprises at least three sequences.

8. The method of claim 1, wherein said set of known biopolymer sequences comprises amino acid sequences.

9. The method of claim 1, wherein said set of known biopolymer sequences comprises nucleic acid sequences.

10. The method of claim 1, wherein said set of known biopolymer sequences comprises genomic nucleic acid sequences.

11. The method of claim 1, wherein said set of known biopolymer sequences comprises non-coding regions.

12. The method of claim 1, wherein said set of known biopolymer sequences comprises regulatory regions.

13. The method of claim 1, wherein said set of known biopolymer sequences comprises a plurality of transcriptional regulatory regions.

14. The method of claim 1, wherein said distribution of monomers at a first node is different from said distribution of monomers at a second node.

15. The method of claim 1, wherein one of said scoring matrices is a function of independent probabilities of a monomer occurrence.

16. The method of claim 1, wherein said set at known biopolymer sequences comprises prohormones.

* * * * *